US009516166B1

(12) United States Patent
Clawson

(10) Patent No.: US 9,516,166 B1
(45) Date of Patent: Dec. 6, 2016

(54) CHEMICAL SUICIDE PROTOCOL FOR EMERGENCY RESPONSE

(71) Applicant: Jeffrey J. Clawson, Salt Lake City, UT (US)

(72) Inventor: Jeffrey J. Clawson, Salt Lake City, UT (US)

(*) Notice: Subject to any disclaimer, the term of this patent is extended or adjusted under 35 U.S.C. 154(b) by 0 days.

(21) Appl. No.: 14/723,947

(22) Filed: May 28, 2015

(51) Int. Cl.
*H04M 11/00* (2006.01)
*H04M 3/51* (2006.01)
*H04M 1/725* (2006.01)
*H04W 4/22* (2009.01)

(52) U.S. Cl.
CPC ....... *H04M 3/5116* (2013.01); *H04M 1/72541* (2013.01); *H04W 4/22* (2013.01)

(58) Field of Classification Search
None
See application file for complete search history.

(56) References Cited

U.S. PATENT DOCUMENTS

| | | | |
|---|---|---|---|
| 3,799,147 A | 3/1974 | Adolph et al. |
| 4,130,881 A | 12/1978 | Haessler et al. |
| 4,164,320 A | 8/1979 | Irazoqui et al. |
| 4,237,344 A | 12/1980 | Moore |
| 4,290,114 A | 9/1981 | Sinay |
| 4,338,493 A | 7/1982 | Stenhuis et al. |
| 4,360,345 A | 11/1982 | Hon |
| 4,455,548 A | 6/1984 | Burnett |
| 4,489,387 A | 12/1984 | Lamb et al. |
| 4,731,725 A | 3/1988 | Suto et al. |

(Continued)

FOREIGN PATENT DOCUMENTS

| | | |
|---|---|---|
| CN | 1674685 A | 9/2005 |
| CN | 101169840 A | 4/2008 |

(Continued)

OTHER PUBLICATIONS

Non-Final Office Action, for U.S. Appl. No. 14/169,302, filed Jan. 31, 2014, and mailed from the USPTO on Sep. 25, 2015, 46 pgs.

(Continued)

*Primary Examiner* — Stella Woo
(74) *Attorney, Agent, or Firm* — Stoel Rives LLP

(57) ABSTRACT

Systems and methods are provided to guide an emergency dispatcher in responding to emergency calls involving a possible chemical suicide. The systems and methods can include an emergency medical dispatch protocol configured to facilitate rapid, uniform, and consistent handling of events involving a possible chemical suicide. The emergency medical dispatch protocol includes one or more dispatch protocols configured for particular incidents or emergency situations, such as to aid the dispatcher in processing calls relating to chemical suicides. The emergency medical dispatch protocol presents a pre-scripted interrogation, including preprogrammed inquiries for a dispatcher to ask the caller. The pre-scripted interrogation of the dispatch protocol facilitates rapid, uniform, and consistent responses to incidents with chemical suicide. The dispatch protocol may utilize a diagnostic tool to evaluate the likelihood of a chemical suicide, increase scene safety, and facilitate deployment of responders as quickly as possible.

22 Claims, 8 Drawing Sheets

(56) References Cited

U.S. PATENT DOCUMENTS

| | | | |
|---|---|---|---|
| 4,839,822 | A | 6/1989 | Dormond et al. |
| 4,858,121 | A | 8/1989 | Barber et al. |
| 4,865,549 | A | 9/1989 | Sonsteby |
| 4,922,514 | A | 5/1990 | Bergeron et al. |
| 4,926,495 | A | 5/1990 | Comroe et al. |
| 4,945,476 | A | 7/1990 | Bodick et al. |
| 4,967,754 | A | 11/1990 | Rossi |
| 5,063,522 | A | 11/1991 | Winters |
| 5,065,315 | A | 11/1991 | Garcia |
| 5,072,383 | A | 12/1991 | Brimm et al. |
| 5,077,666 | A | 12/1991 | Brimm et al. |
| 5,086,391 | A | 2/1992 | Chambers |
| 5,109,399 | A | 4/1992 | Thompson |
| 5,122,959 | A | 6/1992 | Nathanson et al. |
| 5,193,855 | A | 3/1993 | Shamos |
| 5,228,449 | A | 7/1993 | Christ et al. |
| 5,253,164 | A | 10/1993 | Holloway et al. |
| 5,255,187 | A | 10/1993 | Sorensen |
| 5,291,399 | A | 3/1994 | Chaco |
| 5,323,444 | A | 6/1994 | Ertz et al. |
| 5,339,351 | A | 8/1994 | Hoskinson et al. |
| 5,348,008 | A | 9/1994 | Bornn et al. |
| 5,379,337 | A | 1/1995 | Castillo et al. |
| 5,404,292 | A | 4/1995 | Hendrickson |
| 5,410,471 | A | 4/1995 | Alyfuku et al. |
| 5,423,061 | A | 6/1995 | Fumarolo et al. |
| 5,438,996 | A | 8/1995 | Kemper et al. |
| 5,441,047 | A | 8/1995 | David et al. |
| 5,462,051 | A | 10/1995 | Oka et al. |
| 5,471,382 | A | 11/1995 | Tallman et al. |
| 5,502,726 | A | 3/1996 | Fischer |
| 5,513,993 | A | 5/1996 | Lindley et al. |
| 5,516,702 | A | 5/1996 | Senyei et al. |
| 5,521,812 | A | 5/1996 | Feder et al. |
| 5,536,084 | A | 7/1996 | Curtis et al. |
| 5,544,649 | A | 8/1996 | David et al. |
| 5,554,031 | A | 9/1996 | Moir et al. |
| 5,590,269 | A | 12/1996 | Kruse et al. |
| 5,594,638 | A | 1/1997 | Iliff |
| 5,594,786 | A | 1/1997 | Chaco et al. |
| 5,596,994 | A | 1/1997 | Bro |
| 5,630,125 | A | 5/1997 | Zellweger |
| 5,636,873 | A | 6/1997 | Sonsteby |
| 5,650,995 | A | 7/1997 | Kent |
| 5,660,176 | A | 8/1997 | Iliff |
| 5,675,372 | A | 10/1997 | Aguayo, Jr. et al. |
| 5,682,419 | A | 10/1997 | Grube et al. |
| 5,684,860 | A | 11/1997 | Milani et al. |
| 5,689,229 | A | 11/1997 | Chaco et al. |
| 5,719,918 | A | 2/1998 | Serbetciouglu et al. |
| 5,722,418 | A | 3/1998 | Bro |
| 5,724,983 | A | 3/1998 | Selker et al. |
| 5,734,706 | A | 3/1998 | Windsor et al. |
| 5,745,532 | A | 4/1998 | Campana, Jr. |
| 5,748,907 | A | 5/1998 | Crane |
| 5,754,960 | A | 5/1998 | Downs et al. |
| 5,759,044 | A | 6/1998 | Redmond |
| 5,761,278 | A | 6/1998 | Pickett et al. |
| 5,761,493 | A | 6/1998 | Blakeley et al. |
| 5,764,923 | A | 6/1998 | Tallman et al. |
| 5,787,429 | A | 7/1998 | Nikolin, Jr. |
| 5,805,670 | A | 9/1998 | Pons et al. |
| 5,809,493 | A | 9/1998 | Ahamed et al. |
| 5,822,544 | A | 10/1998 | Chaco et al. |
| 5,823,948 | A | 10/1998 | Ross, Jr. et al. |
| 5,826,077 | A | 10/1998 | Blakeley et al. |
| 5,832,187 | A | 11/1998 | Pedersen et al. |
| 5,842,173 | A | 11/1998 | Strum et al. |
| 5,844,817 | A | 12/1998 | Lobley et al. |
| 5,850,611 | A | 12/1998 | Krebs |
| 5,857,966 | A * | 1/1999 | Clawson ............... H04M 11/00 600/300 |
| 5,901,214 | A | 5/1999 | Shaffer et al. |
| 5,902,234 | A | 5/1999 | Webb |
| 5,910,987 | A | 6/1999 | Ginter et al. |
| 5,912,818 | A | 6/1999 | McGrady et al. |
| 5,915,019 | A | 6/1999 | Ginter et al. |
| 5,926,526 | A | 7/1999 | Rapaport et al. |
| 5,933,780 | A | 8/1999 | Connor et al. |
| 5,961,446 | A | 10/1999 | Beller et al. |
| 5,962,891 | A | 10/1999 | Arai |
| 5,964,700 | A | 10/1999 | Tallman et al. |
| 5,986,543 | A | 11/1999 | Johnson |
| 5,989,187 | A * | 11/1999 | Clawson ............... G06F 19/325 128/903 |
| 5,991,730 | A | 11/1999 | Lubin et al. |
| 5,991,751 | A | 11/1999 | Rivette et al. |
| 6,004,266 | A * | 12/1999 | Clawson ............... G06F 19/327 128/903 |
| 6,010,451 | A * | 1/2000 | Clawson ............... G06F 19/325 128/920 |
| 6,022,315 | A | 2/2000 | Iliff |
| 6,035,187 | A | 3/2000 | Franza |
| 6,040,770 | A | 3/2000 | Britton |
| 6,052,574 | A | 4/2000 | Smith, Jr. |
| 6,053,864 | A * | 4/2000 | Clawson ............... G06Q 10/00 128/920 |
| 6,058,179 | A | 5/2000 | Shaffer et al. |
| 6,074,345 | A | 6/2000 | van Oostrom et al. |
| 6,076,065 | A * | 6/2000 | Clawson ............... G06Q 50/22 379/45 |
| 6,078,894 | A | 6/2000 | Clawson et al. |
| 6,106,459 | A | 8/2000 | Clawson |
| 6,112,083 | A | 8/2000 | Sweet et al. |
| 6,115,646 | A | 9/2000 | Fiszman et al. |
| 6,117,073 | A | 9/2000 | Jones et al. |
| 6,118,866 | A | 9/2000 | Shtivelman |
| 6,127,975 | A | 10/2000 | Maloney |
| 6,134,105 | A | 10/2000 | Lueker |
| 6,292,542 | B1 | 9/2001 | Bilder |
| 6,370,234 | B1 | 4/2002 | Kroll |
| 6,535,121 | B2 | 3/2003 | Matheny |
| 6,594,634 | B1 | 7/2003 | Hampton et al. |
| 6,607,481 | B1 * | 8/2003 | Clawson ............... G06Q 50/22 128/897 |
| 6,610,012 | B2 | 8/2003 | Mault |
| 6,696,956 | B1 | 2/2004 | Uchida et al. |
| 6,879,819 | B2 | 4/2005 | Brooks |
| 6,901,397 | B1 | 5/2005 | Moldenhauer et al. |
| 6,931,112 | B1 | 8/2005 | McFarland et al. |
| 6,968,375 | B1 | 11/2005 | Brown |
| 7,106,835 | B2 | 9/2006 | Saalsaa |
| 7,194,395 | B2 | 3/2007 | Genovese |
| 7,289,944 | B1 | 10/2007 | Genovese |
| 7,428,301 | B1 * | 9/2008 | Clawson ............... H04M 3/5116 379/265.01 |
| 7,436,937 | B2 * | 10/2008 | Clawson ............... H04M 11/04 379/45 |
| 7,645,234 | B2 | 1/2010 | Clawson |
| 7,703,020 | B2 | 4/2010 | Bhattaru |
| 7,783,586 | B2 | 8/2010 | Friedlander et al. |
| 7,978,826 | B2 | 7/2011 | Salafia et al. |
| 8,066,638 | B2 * | 11/2011 | Clawson ............... G06F 19/3425 128/920 |
| 8,081,951 | B1 | 12/2011 | Blum |
| 8,103,523 | B2 | 1/2012 | Clawson |
| 8,294,570 | B2 | 10/2012 | Clawson |
| 8,335,298 | B2 * | 12/2012 | Clawson ............... G06F 19/3493 128/904 |
| 8,346,942 | B2 | 1/2013 | Ezerzer et al. |
| 8,355,483 | B2 * | 1/2013 | Clawson ............... H04M 11/04 128/904 |
| 8,396,191 | B2 * | 3/2013 | Clawson ............... H04M 3/493 379/201.01 |
| 8,417,533 | B2 * | 4/2013 | Clawson ............... G06Q 10/04 379/45 |
| 8,488,748 | B2 * | 7/2013 | Clawson ............... G06F 19/30 379/37 |
| 8,494,868 | B2 | 7/2013 | Saalsaa |
| 8,670,526 | B2 | 3/2014 | Clawson |
| 8,712,020 | B2 * | 4/2014 | Clawson ............... H04M 3/5116 379/265.01 |

(56) References Cited

U.S. PATENT DOCUMENTS

| | | | |
|---|---|---|---|
| 8,873,719 B2* | 10/2014 | Clawson | H04M 3/493 379/201.01 |
| 8,971,501 B2 | 3/2015 | Clawson et al. | |
| 2002/0004729 A1 | 1/2002 | Zak et al. | |
| 2002/0106059 A1 | 8/2002 | Kroll et al. | |
| 2003/0028536 A1 | 2/2003 | Singh et al. | |
| 2003/0050538 A1 | 3/2003 | Naghavi et al. | |
| 2003/0187615 A1 | 10/2003 | Epler | |
| 2003/0195394 A1 | 10/2003 | Saalsaa | |
| 2003/0211856 A1 | 11/2003 | Zilliacus | |
| 2003/0212575 A1 | 11/2003 | Saalsaa et al. | |
| 2005/0015115 A1 | 1/2005 | Sullivan et al. | |
| 2005/0065813 A1 | 3/2005 | Mishelevich et al. | |
| 2006/0059423 A1 | 3/2006 | Lehmann et al. | |
| 2006/0122520 A1 | 6/2006 | Banet et al. | |
| 2006/0152372 A1* | 7/2006 | Stout | A61B 5/0002 340/573.1 |
| 2006/0167346 A1 | 7/2006 | Sarel | |
| 2006/0173500 A1 | 8/2006 | Walker et al. | |
| 2006/0178908 A1 | 8/2006 | Rappaport | |
| 2006/0212315 A1 | 9/2006 | Wiggins | |
| 2006/0225213 A1 | 10/2006 | Tomcany | |
| 2007/0055559 A1* | 3/2007 | Clawson | G06Q 10/04 705/325 |
| 2007/0112275 A1 | 5/2007 | Cooke et al. | |
| 2007/0116189 A1 | 5/2007 | Clawson | |
| 2007/0189480 A1 | 8/2007 | Salafia et al. | |
| 2007/0201664 A1 | 8/2007 | Salafia et al. | |
| 2008/0208801 A1 | 8/2008 | Friedlander et al. | |
| 2008/0310600 A1 | 12/2008 | Clawson | |
| 2009/0037374 A1 | 2/2009 | Delia et al. | |
| 2009/0168975 A1 | 7/2009 | Clawson | |
| 2009/0191529 A1 | 7/2009 | Mozingo et al. | |
| 2009/0233631 A1 | 9/2009 | Butler, Sr. et al. | |
| 2009/0276489 A1 | 11/2009 | Ragno et al. | |
| 2010/0004710 A1 | 1/2010 | Kellum | |
| 2010/0121156 A1 | 5/2010 | Yoo | |
| 2010/0152800 A1 | 6/2010 | Walker et al. | |
| 2010/0198755 A1 | 8/2010 | Soll et al. | |
| 2010/0257250 A1 | 10/2010 | Salafia et al. | |
| 2011/0050417 A1 | 3/2011 | Piccioni | |
| 2011/0064204 A1* | 3/2011 | Clawson | H04M 11/04 379/45 |
| 2011/0066002 A1* | 3/2011 | Clawson | G06F 19/3493 600/300 |
| 2011/0099031 A1 | 4/2011 | Nair | |
| 2011/0205052 A1 | 8/2011 | Clawson | |
| 2011/0215930 A1 | 9/2011 | Lee | |
| 2012/0066345 A1 | 3/2012 | Rayan et al. | |
| 2012/0171989 A1 | 7/2012 | Matsuo et al. | |
| 2012/0183128 A1 | 7/2012 | Clawson | |
| 2012/0207286 A1 | 8/2012 | Clawson | |
| 2012/0210271 A1 | 8/2012 | Clawson | |

FOREIGN PATENT DOCUMENTS

| | | |
|---|---|---|
| CN | 201117055 Y | 9/2008 |
| CN | 102714524 A | 10/2012 |
| EP | 2476092 A1 | 3/2011 |
| GB | 2471960 | 1/2011 |
| GB | 2478171 A | 8/2011 |
| GB | 2482741 A | 2/2012 |
| GB | 2489875 A | 10/2012 |
| JP | 2002-049693 | 2/2002 |
| JP | 2003-109162 A | 4/2003 |
| JP | 2003-187003 A | 7/2003 |
| JP | 2003-256963 A | 12/2003 |
| JP | 2010-033201 A | 12/2010 |
| KR | 10-2005-0085778 | 8/2005 |
| KR | 10-2006-0084866 | 7/2006 |
| KR | 2007-0043337 A | 4/2007 |
| KR | 10-2008-0004125 | 1/2008 |
| KR | 10-2009-0014837 A | 2/2009 |
| WO | WO2004/030259 | 4/2004 |
| WO | WO 2005/039406 A1 | 5/2005 |
| WO | WO2006/015229 A2 | 2/2006 |
| WO | WO 2008/014398 A2 | 1/2008 |
| WO | WO2008/156876 A1 | 12/2008 |
| WO | WO2011/031383 | 3/2011 |
| WO | WO2012/108898 A1 | 8/2012 |

OTHER PUBLICATIONS

Office Action Summary from USPTO for U.S. Appl. No. 10/140,635 mailed Jul. 16, 2004, 11 pgs.
Office Action Summary from USPTO for U.S. Appl. No. 10/140,635 mailed Apr. 19, 2005, 11 pgs.
Office Action Summary from USPTO for U.S. Appl. No. 10/140,635 mailed Jan. 17, 2006, 13 pgs.
Office Action Summary from USPTO for U.S. Appl. No. 10/140,635 mailed Sep. 20, 2006, 15 pgs.
Office Action Summary from USPTO for U.S. Appl. No. 10/140,635 mailed Jun. 21, 2007, 15 pgs.
International Search Report for PCT/US2008/054987 filed on Feb. 26, 2008, and mailed on Oct. 8, 2008, 2 pgs.
Written Opinion of the International Searching Authority for PCT/US2008/054987 filed on Feb. 26, 2008, and mailed on Oct. 8, 2008, 9 pgs.
Notification of Transmittal of the International Search Report (2 pgs.) for PCT/US2009/040909, International Search Report, (2 pgs.), and Written Opinion (8 pgs.) mailed from International Searching Authority on Jun. 10, 2009.
International Search Report and Written Opinion for PCT/US09/48577, International filing date Jun. 25, 2009, mailed from ISA Aug. 7, 2009, 9 pgs.
International Search Report and Written Opinion mailed Jan. 19, 2011 in PCT Application No. PCT/US2010/043308, filed Jul. 27, 2010.
International Search Report and Written Opinion mailed Jan. 19, 2011 in PCT Application No. PCT/US2010/043311, filed Jul. 27, 2010.
Office Action Summary from USPTO for U.S. Appl. No. 12/396,201 mailed Mar. 8, 2011, 23 pgs.
International Search Report and Written Opinion PCT/US2010/050402, filed on Sep. 27, 2010, and mailed from ISA on Apr. 27, 2011, 9 pgs.
Office Action Summary from USPTO for U.S. Appl. No. 12/268,963 mailed Jul. 29, 2011, 18 pgs.
International Preliminary Report of Patentability for PCT/US2009/048577 filed on Jun. 25, 2009 mailed Oct. 27, 2011, 7 pgs.
International Search Report and Written Opinion for PCT/US2011/042543 filed on Jun. 30, 2011, mailed from ISA on Feb. 9, 2012, 11 pgs.
International Search Report and Written Opinion for PCT/US2011/042582 filed on Jun. 30, 2011, mailed from ISA on Feb. 9, 2012, 8 pgs.
International Preliminary Report of Patentability for PCT/US2010/043308 filed on Jul. 27, 2010 mailed Mar. 22, 2012, 6 pgs.
International Preliminary Report of Patentability for PCT/US2010/043311 filed on Jul. 27, 2010 mailed Mar. 29, 2012, 6 pgs.
Office Action Summary from USPTO for U.S. Appl. No. 12/558,045 mailed Mar. 22, 2012, 9 pgs.
Office Action Summary from USPTO for U.S. Appl. No. 12/558,808 mailed Apr. 23, 2012, 9 pgs.
Office Action Summary from USPTO for U.S. Appl. No. 12/422,561 mailed Jul. 3, 2012, 21 pgs.
International Search Report and Written Opinion for PCT/US2012/021867 filed on Jan. 19, 2012, and mailed from ISA on Aug. 30, 2012, 8 pgs.
Office Action Summary from USPTO for U.S. Appl. No. 13/354,116 mailed Jan. 22, 2013, 9 pgs.
Office Action Summary from USPTO for U.S. Appl. No. 12/422,561 mailed Feb. 1, 2013, 26 pgs.
Notice of Allowance from USPTO for U.S. Appl. No. 13/026,055 mailed Jan. 24, 2013.
Notice of Allowance from USPTO for U.S. Appl. No. 10/255,901 mailed Feb. 20, 2013.

(56) References Cited

OTHER PUBLICATIONS

Nordberg, Marie, "Dispatch Disasters," Emergency Medicine, Aug. 1995.
Notice of Allowance from USPTO for U.S. Appl. No. 13/354,116 mailed Jun. 7, 2013.
Liferidge, Aisha T., et al., "Ability of Laypersons to Use the Cincinnati Prehospital Stroke Scale", Prehospital Emergency Care, Elsevier, vol. 8, No. 4, Oct. 1, 2004, pp. 384-387.
Office Action Summary from USPTO for U.S. Appl. No. 13/026,043 mailed Oct. 10, 2013.
International Preliminary Report of Patentability for PCT/US2011/042543 filed on Jun. 30, 2011 mailed Aug. 22, 2013, 7 pgs.
International Preliminary Report of Patentability for PCT/US2011/042582 filed on Jun. 30, 2011 mailed Aug. 22, 2013, 5 pgs.
Office Action Summary from USPTO for U.S. Appl. No. 13/605,501 mailed Nov. 18, 2013.
International Search Report and Written Opinion for PCT/US2013/055537 filed on Aug. 19, 2013 and mailed from ISA on Nov. 22, 2013.
Notice of Allowance from USPTO for U.S. Appl. No. 13/026,043 mailed Jan. 13, 2014.
Nor, A. Mohd, et al., "Agreement Between Ambulance Paramedic- and Physician-Recorded Neurological Signs With Face Arm Speech Test (FAST) in Acute Stroke Patients", http://stroke.ahajournals.org/content/35/6/1355, Apr. 29, 2004, visited Nov. 17, 2013, 3 pgs.
Clark University "Active Shooter Emergency Plan" Revised Jan. 11, 2013.
Notice of Allowance from USPTO for U.S. Appl. No. 13/605,501 mailed Mar. 6, 2014.
International Search Report and Written Opinion for PCT/US2014/011405 filed on Jan. 14, 2014 and mailed from ISA on Apr. 25, 2014.
International Search Report and Written Opinion for PCT/US2014/014029 filed on Jan. 31, 2014 and mailed from ISA on May 16, 2014.
Office Action Summary from USPTO for U.S. Appl. No. 13/755,793 mailed Jul. 21, 2014.
International Preliminary Report of Patentability for PCT/US2013/055537 filed on Aug. 19, 2013 mailed Mar. 19, 2015.
Notice of Allowance from USPTO for U.S. Appl. No. 12/422,561 mailed Dec. 9, 2014.
Notice of Allowance from USPTO for U.S. Appl. No. 13/755,793 mailed Sep. 22, 2014.
Radosevich, Lynda, "Network holds sway on life, death," Computerworld, v27 n21, May 24, 1993, 2 pgs.
Harris, Roger, "Updated 911 Phone System Top Concern of Residents," Business First-Louisville, v9 n19 s1, Dec. 1992, 3 pgs.
"Geac Completes Software Install," Wireless Week, Nov. 18, 1996, 3 pgs.
"Dictaphone introduces Windows-based Computer-Aided Dispatch (CAD) system," Business Wire, Apr. 23, 1996, 2 pgs. (in commercial use in 1995).
Holroyd, Brian, et al., "Medical Control; Quality Assurance in Prehospital Care," JAMA, the Journal of American Medical Association, v256, n8, Aug. 1986, p. 1027-1031.
CBS web page News Story entitled "911 Operator: 'It's got to be Hell'", Mar. 31, 2006 (excerpts from 911 operators' actions during the attacks on Sep. 11, 2001), 3 pgs.
Best, Wendy, "999 United Emergency services share life-saving Role to boost response," Western Daily Press, WDP Severnside ed., May 27, 1999, 2 pgs.
Poellmitz, William C., "Wireless technology keeps public safety a step ahead," Nation's Cities Weekly, v21 n17, Apr. 27, 1998, 3 pgs.
Crowley, Mark, "Learning from CAD System Implementation," Communications, v29 n8, Aug. 1992, 5 pgs.
Anonymous, "Suburban Chicago towns centralize 911 services," Communications News, v31 n10, Oct. 1994, 2 pgs.
Office Action Summary from USPTO for U.S. Appl. No. 10/255,901 mailed Dec. 31, 2003, 8 pgs.
Office Action Summary from USPTO for U.S. Appl. No. 10/255,901 mailed Oct. 13, 2004, 8 pgs.
Office Action Summary from USPTO for U.S. Appl. No. 10/255,901 mailed Jun. 29, 2005, 7 pgs.
Advisory Action Before the Filing of an Appeal Brief from USPTO for U.S. Appl. No. 10/255,901 mailed Feb. 14, 2006, 3 pgs.
Office Action Summary from USPTO for U.S. Appl. No. 10/255,901 mailed Jun. 7, 2006, 8 pgs.
Office Action Summary from USPTO for U.S. Appl. No. 10/255,901 mailed Feb. 27, 2007, 8 pgs.
Office Action Summary from USPTO for U.S. Appl. No. 10/255,901 mailed Sep. 6, 2007, 9 pgs.
Office Action Summary from USPTO for U.S. Appl. No. 10/255,905 mailed May 19, 2004, 7 pgs.
Office Action Summary from USPTO for U.S. Appl. No. 10/255,905 mailed May 26, 2005, 5 pgs.
Office Action Summary from USPTO for U.S. Appl. No. 10/255,905 mailed Feb. 9, 2006, 8 pgs.
Advisory Action Before the Filing of an Appeal Brief from USPTO for U.S. Appl. No. 10/255,905 mailed Aug. 11, 2006, 3 pgs.
Office Action Summary from USPTO for U.S. Appl. No. 10/255,905 mailed Jan. 30, 2007, 7 pgs.
Notice of Non-Compliant Amendment (37 CFR 1.121) from USPTO for U.S. Appl. No. 10/255,905 mailed Jul. 9, 2007, 4 pgs.
Office Action Summary from USPTO for U.S. Appl. No. 10/255,905 mailed Oct. 5, 2007, 7 pgs.
Office Action Summary from USPTO for U.S. Appl. No. 09/685,697 mailed Jul. 18, 2003, 8 pgs.
Office Action Summary from USPTO for U.S. Appl. No. 09/685,697 mailed Feb. 3, 2004, 5 pgs.
Office Action Summary from USPTO for U.S. Appl. No. 09/685,697 mailed Jan. 4, 2005, 5 pgs.
Office Action Summary from USPTO for U.S. Appl. No. 09/685,697 mailed Oct. 4, 2005, 7 pgs.
Advisory Action Before the Filing of an Appeal Brief from USPTO for U.S. Appl. No. 09/685,697 mailed Mar. 13, 2006, 4 pgs.
Office Action Summary from USPTO for U.S. Appl. No. 09/685,697 mailed Jun. 26, 2006, 8 pgs.
Office Action Summary from USPTO for U.S. Appl. No. 09/685,697 mailed Apr. 10, 2007, 9 pgs.
Office Action Summary from USPTO for U.S. Appl. No. 09/685,697 mailed Oct. 9, 2007, 11 pgs.
Office Action Summary from USPTO for U.S. Appl. No. 10/140,635 mailed Oct. 3, 2003, 9 pgs.
Notice of Allowance and Fee(s) Due for U.S. Appl. No. 14/169,302, filed Jan. 31, 2014, and mailed from the USPTO on Mar. 4, 2016, 13 pgs.
Notice of Allowance and Fee(s) Due for U.S. Appl. No. 15/083,810, filed Mar. 29, 2016, and mailed from the USPTO on Sep. 23, 2016, 14 pgs.
Non-Final Office Action for U.S. Appl. No. 15/083,810, filed Mar. 29, 2016, and mailed from the USPTO on Jul. 15, 2016, 28 pgs.
International Search Report and Written Opinion for PCT/US16/25822 filed on Apr. 4, 2016 and mailed from ISA on May 3, 2016 10 pgs.

* cited by examiner

CHEMICAL SUICIDE PROTOCOL FOR EMERGENCY RESPONSE

COPYRIGHT NOTICE

© 2015 Priority Dispatch Corp. on assignment. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR §1.71(d).

TECHNICAL FIELD

The present disclosure relates to computer systems and methods for providing emergency protocol interrogation, instruction, and dispatch. More specifically, the disclosure is directed to computer-implemented protocols to enable a dispatcher to process emergency calls in an accurate, consistent, and systematic manner by guiding the dispatcher during interrogation and instruction of an emergency caller.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION OF PREFERRED EMBODIMENTS

Figure 1:
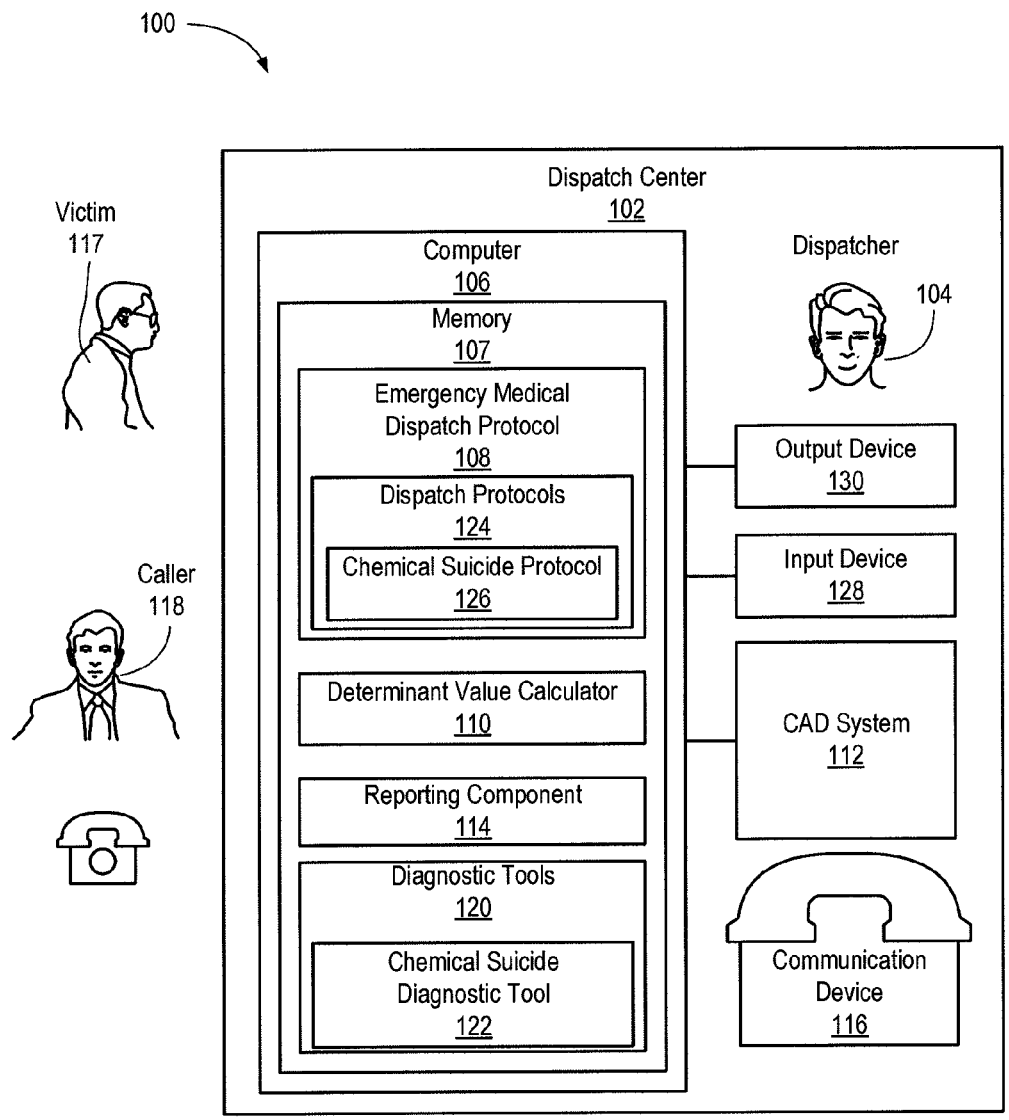
FIG. 1 illustrates a block diagram of an emergency medical dispatch system, according to one embodiment.

Suicide by inhaling poisonous vapors that can be created from a mixture of household chemicals is commonly referred to as chemical suicide. Chemical suicide not only is harmful to the victim, but also may be hazardous to an unknowing passerby, emergency responders, and any others who may come in contact with the poisonous vapors.

Emergency dispatchers are often the first emergency personnel to receive information concerning an incident. In their role of receiving emergency calls, an emergency dispatchers are in a unique position to potentially be the first to identify and/or report a chemical suicide. By identifying a chemical suicide, a dispatcher may take steps and provide instructions to improve scene safety for the caller and emergency responders. Unfortunately, often emergency dispatchers are inexperienced and unskilled, largely due to a high turnover rate among emergency dispatchers.

Emergency dispatchers handle emergency calls reporting a wide variety of emergency situations. An automated emergency dispatch system, potentially implemented on a computer, can aid even an unskilled and inexperienced dispatcher in prioritizing emergency calls that are received and in processing the calls to generate an appropriate emergency dispatch response. Regardless of the experience or skill level of the dispatcher, the automated emergency dispatch system can enable a consistent and predictable emergency dispatch response, despite the diverse aspects of emergency situations that may be reported from one call to the next.

Although an automated emergency dispatch system can enable receiving and processing of widely divergent aspects of emergency situations, these systems may not be well suited for processing particular types of unique situations. More particularly, an automated emergency dispatch system may not be well suited to gathering and assessing factors that may be indicative of a chemical suicide. An emergency situation possibly involving chemical suicide may be hazardous to an unknowing passerby. Additional interrogation and instructions, and/or alternative emergency dispatch procedures or protocols may improve safety at a possibly dangerous scene, and facilitate gathering information that can be used in identifying a chemical suicide.

Existing automated emergency dispatch systems are not equipped to assist or enable a dispatcher to process an emergency call involving a chemical suicide. A dispatcher unfamiliar with chemical suicide incidents and/or untrained in handling them may not be able to compensate for the shortcomings of an automated emergency dispatch system. Inexperienced and/or unskilled dispatchers are generally unable to initiate or assist a proper medical response, or to provide effective advice to callers. Even highly skilled and experienced dispatchers may have little skill or experience with handling incidents involving chemical suicide, simply because such incidents may be relatively rare compared to other types of incidents that are reported. Accordingly, the present disclosure provides a method and system for processing of emergency calls involving chemical suicides in a rapid, consistent, and predictable manner.

The embodiments of the disclosure will be best understood by reference to the drawings, wherein like parts are designated by like numerals throughout. It will be readily understood that the components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified.

In some cases, well-known features, structures, or operations are not shown or described in detail. Furthermore, the described features, structures, or operations may be combined in any suitable manner in one or more embodiments. It will also be readily understood that the components of the embodiments as generally described and illustrated in the figures herein could be arranged and designed in a wide variety of different configurations.

Several aspects of the embodiments described will be illustrated as software modules or components. As used herein, a software module or component may include any type of computer instruction or computer-executable code located within a memory device and/or computer-readable storage medium. A software module may, for instance, comprise one or more physical or logical blocks of computer instructions, which may be organized as a routine, program, object, component, data structure, etc. that performs one or more tasks or implements particular abstract data types.

In certain embodiments, a particular software module may comprise disparate instructions stored in different locations of a memory storage device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools.

An emergency dispatch system as disclosed herein may be computer-implemented in whole or in part on a digital computer. The digital computer includes a processor performing the required computations. The computer further includes a memory in electronic communication with the processor to store a computer operating system. The computer operating systems may include, but are not limited to, MS-DOS, Windows, Linux, Unix, AIX, CLIX, QNX, OS/2, and Apple. Alternatively, it is expected that future embodiments will be adapted to execute on other future operating systems. The memory may also store application programs including a Computer Aided Dispatch (CAD) program, an automated emergency dispatch protocol, and a user interface program. The memory may also include data storage. The computer may further include an output device, such as a display unit, for viewing the displayed instructions and inquiries, and a user input device for inputting response data.

FIG. 1 illustrates an emergency medical dispatch system 100, according to one embodiment. At a dispatch center 102, a dispatcher 104 may operate a computer 106 or other computing device. The computer 106 may include a memory 107 to store protocols, modules, tools, data, etc. The computer 106 may be configured to follow an emergency medical dispatch protocol 108 to enable the dispatcher 104 to rapidly and consistently address an emergency incident involving a crime or requiring medical assistance, as reported by a caller 118. An emergency call requesting law enforcement or medical attention may report an incident that may involve a victim 117. As can be appreciated, in some circumstances and/or incidents, the caller 118 is the victim 117. In other instances the caller 118 may be a second party (e.g., a person with the victim 117), third party (e.g., a person not in the immediate vicinity of the victim 117), fourth party (e.g., a reporting or referral agency), or the suspect (or perpetrator). The emergency medical dispatch protocol 108 may include a logic tree, preprogrammed inquiries or questions, possible responses from a caller 118 to the inquiries, and instructions to the caller 118. The responses may route to subsequent preprogrammed inquiries and/or instructions to the caller 118. The emergency medical dispatch protocol 108 may also include dispatch protocols 124 for guiding the dispatcher 104 in processing emergency calls involving specific situations and/or incidents. The dispatch protocols 124 may similarly include a logic tree, preprogrammed inquiries or questions, possible responses from a caller 118 to the preprogrammed inquiries, and instructions for the caller 118. The dispatch protocols 124 may include a chemical suicide protocol 126 for rapid, consistent, and predictable processing of emergency calls involving possible chemical suicide.

The responses of the caller 118 are processed according to predetermined logic of the logic tree of the emergency medical dispatch protocol 108. The predetermined logic may enable the emergency medical dispatch system 100 to provide to the dispatcher 104 information concerning the correct emergency medical dispatch response (e.g., by trained law enforcement officers or agencies and/or other emergency responders). The predetermined logic may also enable the emergency medical dispatch system 100 to provide to the dispatcher 104 appropriate post-dispatch instructions for relay to the caller 118 before professional help arrives at the scene. The predetermined logic may also enable the emergency medical dispatch system 100 to aid the dispatcher in determining an appropriate priority of the emergency call, including but not limited to a priority of the emergency call relative to other emergency calls and a level of emergency response to provide for the reported incident or situation.

Although an emergency medical dispatch system 100 is disclosed and described herein, a person of ordinary skill can appreciate that other emergency dispatch systems and protocols are contemplated, including but not limited to emergency medical dispatch systems and protocols and emergency fire dispatch systems and protocols. Exemplary embodiments of emergency dispatch systems and protocols are disclosed in U.S. Pat. Nos. 5,857,966; 5,989,187; 6,004,266; 6,010,451; 6,053,864; 6,076,065; 6,078,894; 6,106,459; 6,607,481; 7,106,835; 7,428,301; 7,436,937; 7,645,234; 8,066,638; 8,103,523; 8,294,570; 8,335,298; 8,355,483; 8,417,533; 8,488,748; and 8,670,526, which are hereby incorporated herein by reference.

The computer 106 operates a determinant value calculator 110 to calculate a determinant value from the responses of the caller 118 to protocol questions. The determinant value may be selected from a group of pre-established determinant values, such that the emergency responders are familiar with the determinant values and understand the meaning of each and what would be a corresponding emergency response. For example, the determinant values may range from E-1 for generally very serious emergencies to $\Omega$-2 for generally less serious emergencies. The determinant value may provide a categorization code of the type and level of the incident.

In one embodiment of the present disclosure, the determinant value is a combination of a determinant level (Alpha A, Bravo B, Charlie C, Delta D, Echo E and Omega $\Omega$) and a numeric value. Generally, $\Omega$-2 is the least serious while E-1 is the most serious call. Depending on the determinant level, the appropriate emergency response is dispatched as indicated by the response protocol. For example, an Alpha-A call will typically be responded to by a next available law enforcement unit/medical personnel using the safest arrival method reasonably possible. A Delta-D call will typically be responded to by any or all available law enforcement units/medical personnel proceeding under the most urgent method possible. Echo-E calls typically involve likely immediate life-threatening situations and will be responded to in the most urgent manner available. Bravo-B and Charlie-C calls are intermediate calls that are typically responded to in business-like, orderly manner according to specific department protocol. An Omega-Ω call is generally not specifically responded to, but rather is referred to another person or agency. For the purposes of this disclosure, Echo-E is generally abbreviated as E; Delta-D is generally abbreviated as D; Charlie-C is generally abbreviated as C; Bravo-B is generally abbreviated as B; Alpha-A is generally abbreviated as A; and Omega-Ω is generally abbreviated as Ω. Generally, the lower determinant levels (e.g., numbers) within a determinant classification are more urgent than higher numbers. For example, an emergency dispatch call with a determinant value of D-1 is generally more critical, requiring a more urgent response than a call with a determinant value of D-2. However, in some instances, the numeric determinant levels within a determinant value may serve only to identify the type, rather than criticality, of the call. Also, if more than one determinant value can be assigned to a particular call, the more critical or higher determinant value is assigned. That is, the call is assigned a criticality determinant value based on the fact or aspect that would lead to the most urgent response. For example, if the call concerns a burglary that occurred over 30 minutes before, but where the suspect remains on the scene or nearby and the caller indicates that he or she is still in danger and feels his or her life is in imminent danger, then the determinant value assigned would be E-1 (due to the imminent danger) rather than D-2 (suspect on scene or nearby) or B-1 (incident occurred over 30 minutes before).

Many calls for law enforcement and/or medical assistance are not true emergencies, so it is important to prioritize the calls in several ways. First, calls that are true emergencies should be dispatched first. Second, if an agency has units with different capabilities, the emergencies involving more severe problems can be sent units that are more skilled and advanced (e.g., a S.W.A.T. team or bomb squad). And finally, if lights and siren are not needed, they should not be used, thereby increasing the safety of all those on the road and in the emergency response vehicles. The computer 106 presents the determinant value to generate an appropriate emergency dispatch response and/or establish the priority of the emergency call. The response may include dispatching professional law enforcement officers or other emergency responders to the scene of the emergency. The protocols used shall have passed through a rigorous review by a panel of experienced law enforcement agents and EMS public safety experts.

The determinant value may be provided to a Computer Aided Dispatch (CAD) system 112, which is a tool that a dispatcher 104 may use to track and allocate emergency response resources for processing emergency calls. The CAD system 112 may manage dispatcher tools for processing emergency calls, including but not limited to the emergency medical dispatch protocol 108, communication resources (e.g., radio system, alpha pager), mapping tools (e.g., global positioning system (GPS) technology, geographic information systems (GIS)), and vehicle location systems (e.g., automatic vehicle location (AVL)). The CAD system 112 may operate in whole or in part on a separate computer in communication with the computer 106. In another embodiment, the CAD system 112 operates on the computer 106. The primary information used by the CAD system 112 is location information of the incident and units, unit availability, and the type of incident. The CAD system 112 may use third party solutions, such as E-911, vehicle location transponders, and mobile data terminals (MDT's) for automating the location and availability tasks. The CAD system 112 may also use an emergency medical dispatch protocol 108 to facilitate structured call taking for incident interrogation, as previously described.

Although many emergency calls are not true emergencies, all situations can benefit from expert evaluation and pertinent instruction. Prior to the arrival of professional help on-scene, the emergency medical dispatch protocol 108 may provide the dispatcher 104 with instructions for the caller 118 that are appropriate to the type of call, whether the call relates to a complaint of vandalism or to a homicide. These instructions may help expedite the work of law enforcement officers and/or other emergency responders.

The computer 106 may include a reporting component 114 to statistically measure the performance of individual staff and overall performance of the dispatch center 102. To record information received during a call, the dispatcher 104 may be required to open a new case. Once the call is complete, the dispatcher 104 may close the case, and a case summary may be saved. The case summary may be retrieved later for review and/or analysis. The reporting component 114 may determine statistics from the case summaries and/or while the cases are open. The statistics may include compliance rates, call processing statistics, and peer measurements.

The computer 106 may further comprise an input device 128, such as a keyboard, mouse, touch screen, laser pointer, or other input device, and an output device 130, such as a display monitor. The input device 128 receives input from a user (generally a dispatcher 104) and provides the input to the emergency medical dispatch system 100. The input may be provided to the computer 106, the emergency medical dispatch protocol 108, a diagnostic tool 120, and/or the CAD system 112. The output device 130 receives output from the emergency medical dispatch system 100 and displays or otherwise provides the output to the user. In another embodiment, the input device 128 and output device 130 are provided by the CAD system 112.

The dispatch center 102 includes a communication device 116 (e.g., telephone equipment) to answer emergency calls. In some embodiments, the communication device 116 may be coupled to the computer 106 to enable the computer 106 to send and/or receive text messages and/or to identify dual-tone multi-frequency (DTMF) signals received at the communication device 116. A call into the dispatch center 102 from a caller 118 may initiate creation of an emergency call incident. The dispatcher 104 identifies the call as requiring an emergency medical dispatch, and the emergency medical dispatch protocol 108 is accessed. The protocol 108, including the dispatch protocols 124, may provide questions and/or instructions that are expertly drafted to assist a novice caller 118 in reporting aspects of the incident, and/or assessing a situation of a victim 117. The protocol 108 may also provide expertly drafted instructions to assist a victim 117 prior to the arrival of trained law enforcement and/or emergency responders. The instructions may be vocally relayed by the dispatcher 104 to the caller 118 over the communication device 116.

Some protocol inquiries or questions may be readily answerable by the caller 118, whereas others may be more difficult to answer. Certain diagnostic inquiries may be difficult for the untrained caller to determine or may be difficult to answer under the stress of an emergency situation. Accordingly, in addition to instructions, the emergency medical dispatch system 100 may provide one or more computer-implemented diagnostic tools 120. The diagnostic tools 120 may greatly improve information collection and intervention for emergency medical response situations and aid in saving lives.

A diagnostic tool 120 may aid the dispatcher 104 and/or the caller 118 (via instructions from the dispatcher 104) in assessing a situation of a victim 117. A diagnostic tool 120 may also be an interventional tool, providing instructions that direct a caller 118 to intervene, or take action, to aid a victim 117, or otherwise change the circumstances or conditions of an emergency situation. For sake of clarity, diagnostic tools and interventional tools are both referred to herein generally as diagnostic tools. Accordingly, a diagnostic tool 120, as referred to herein, may provide diagnostic instructions, interventional instructions, or both diagnostic and interventional instructions. Whether a diagnostic tool 120 provides merely diagnostic instructions, merely interventional instructions, or both diagnostic and interventional instructions, the diagnostic tool 120 provides consistent and reliable instruction, information gathering, and/or timing for a particular emergency situation.

The diagnostic tools 120 are computer-implemented software modules that enable a dispatcher 104 to provide consistent, expert advice to assist a caller 118 with regards to a particular aspect of an emergency situation, such as determining a vital sign. One benefit of the diagnostic tools 120 is the computer-aided timing of techniques to determine the vital signs. In highly stressful conditions, the diagnostic tools 120 provide a necessary resource for reading critical signs. The diagnostic tools 120 may be stored in the memory of the computer 106 and initiated and executed as required. The diagnostic tools 120 may be embodied as computer-executable software applications and associated data.

The emergency medical dispatch protocol 108, including the dispatch protocols 124, also may call on one or more diagnostic tools 120 to assist with an inquiry and may route to the appropriate diagnostic tool 120 when needed. When directed according to the protocol, the emergency medical dispatch protocol 108 may automatically, i.e., without dispatcher 104 intervention, initiate the appropriate diagnostic tool 120. This may occur when the emergency medical dispatch protocol 108 arrives at a diagnosis or assessment step in the logic tree. The emergency medical dispatch system 100 may also allow the dispatcher 104 the option to call upon a diagnostic tool 120 as desired. Icons may be displayed in a tool bar or other convenient location on a user interface to allow the dispatcher 104 to initiate a corresponding diagnostic tool 120. One particular diagnostic tool 120 discussed herein may be a chemical suicide diagnostic tool 122.

The chemical suicide diagnostic tool 122 may be configured to advance scene safety for the caller 118. By asking specific questions about the scene that do not require the caller 118 to be near the potentially hazardous chemicals, the dispatcher 104 may gather information about the incident without placing the caller 118 in danger. The chemical suicide diagnostic tool 122 may provide a warning that the scene is dangerous. Based on that warning, the dispatcher 104 may advise the caller 118 to evacuate the scene.

The chemical suicide diagnostic tool 122 may also be configured to advise emergency responders that an emergency incident to which they are responding may involve a chemical suicide. Advanced warning that the incident may involve hazardous chemicals enables the emergency responders to take available precautions and to be more alert to potential factors and information that indicate a chemical suicide. The presence of a possible chemical suicide may be communicated through addition of a suffix to the determinant value. Specific details about the chemical suicide, such as the bias category, may be passed to the emergency responders via a dispatcher communication with the responders, which may include a responder script.

The chemical suicide diagnostic tool 122 may be launched from within, or at least in conjunction with, the progression of the emergency medical dispatch protocol 108 and dispatch protocols 124, including the chemical suicide protocol 126, to enhance and supplement emergency call processing facilitated by the emergency medical dispatch protocol 108. The chemical suicide diagnostic tool 122 may be launched automatically by the emergency medical dispatch protocol 108, or launched manually by a dispatcher 104.

Figure 2:
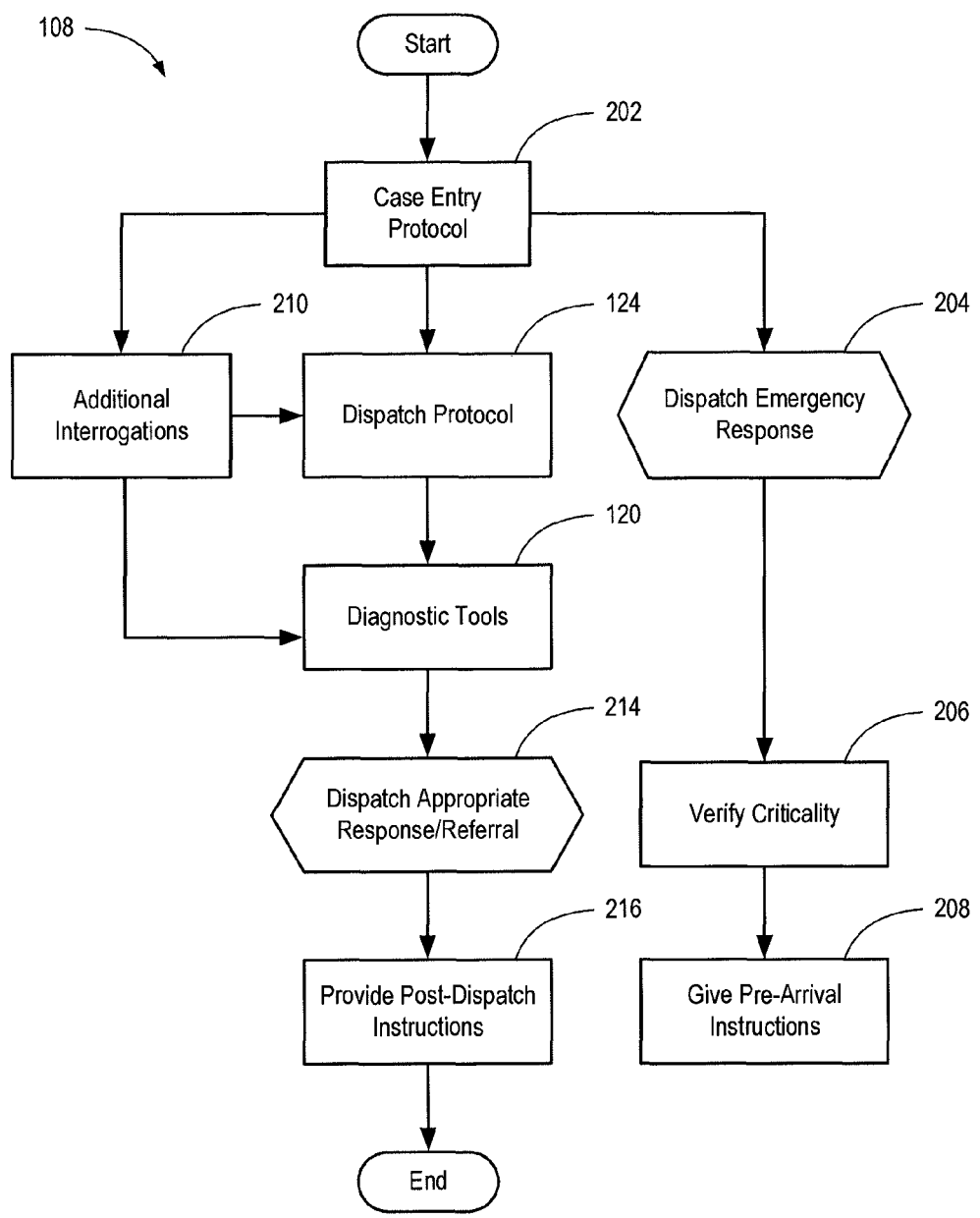
FIG. 2 is a high-level flow diagram of an emergency medical dispatch protocol of an emergency medical dispatch system, according to one embodiment.

FIG. 2 is a high-level flow diagram of an emergency medical dispatch protocol 108 of an emergency medical dispatch system, according to one embodiment. The protocol 108 may begin with a case entry protocol 202 that guides the dispatcher in gathering initial information. One aim of the case entry protocol 202 is to obtain sufficient information from the caller to permit identification of a chief complaint. Also, the case entry protocol 108 may be considered a primary interrogation because all calls may be processed through the case entry protocol 202 to gather initial incident information. The information received through the case entry protocol 202 may include a location of the incident, a call-back number in the event the call is disconnected, the caller's name, and a description of the incident.

If the dispatcher receives and enters information that an incident is especially critical for any reason (e.g., a caller in imminent danger, a sinking vehicle, a vehicle in rising flood water, or a vehicle that cannot stop because of a stuck accelerator), an emergency response is dispatched 204 immediately, before the dispatcher continues with any further interrogation or instructions. The dispatched 204 emergency response may be a maximum emergency response, including properly trained law enforcement officers and medical personnel. The criticality of the incident is verified 206 and pre-arrival instructions are given 208. The pre-arrival instructions can be tailored to the specific incident and/or situation. Typically, a result of properly conveyed (by the dispatcher) and executed (by the caller) pre-arrival instructions may be a more calm, stable situation at the time the emergency responders arrive, and/or reduced risk of injury or death for the caller. The pre-arrival instructions may aid to ensure safety and improve the effectiveness of the dispatched 204 emergency response.

If the dispatcher receives information from the caller to confirm the incident is not critical (e.g., not an imminent danger), but the dispatcher lacks sufficient information to proceed directly to a dispatch protocol 124, the emergency medical dispatch protocol 108 may shunt to additional inquiries 210 designed to guide the dispatcher to gather information from the caller to enable the dispatcher to ascertain the chief complaint. If the chief complaint is determined, the emergency medical dispatch protocol 108 may shunt to the appropriate dispatch protocol 124 for dealing with that chief complaint.

The dispatch protocol 124 may guide the dispatcher through a secondary interrogation focusing on the chief complaint. The dispatch protocol 124 may present a pre-scripted interrogation to enable a more orderly and detailed understanding of the incident that can be communicated to emergency responders. The pre-scripted interrogation may include preprogrammed inquiries focused on gathering information relating to the chief complaint. The preprogrammed inquiries provided by the dispatch protocol 124 may be termed "Key Questions" for the particular situation or condition of the chief complaint. The preprogrammed inquiries presented may depend on caller responses. Dispatch protocols 124 may utilize diagnostic tools 120 to evaluate gathered information.

During the dispatch protocol 124, the dispatcher and/or the emergency medical dispatch protocol 108 will gather, through interrogation, information about the circumstances of the incident or emergency situation, and may dispatch 214 an appropriate emergency dispatch response. The dispatch protocol 124 facilitates uniform and consistent gathering of information relating to the emergency and dispatching of an appropriate emergency dispatch response. The appropriate emergency dispatch response may be determined through a system of assigning determinant values as the protocol progresses (i.e., traverses) through a logic tree. The determinant values, as described above, may range, for example, from E-1 for generally very serious emergencies to Ω-2 for generally less serious emergencies. In another embodiment, the determinant values may range differently, such as for example from A-1 for generally very serious emergencies to E-5 for generally less serious emergencies.

After the appropriate emergency dispatch response has been sent (e.g., law enforcement officers), the dispatcher may remain on the telephone with the caller to provide post-dispatch instructions 216 regarding what to do, and what not to do, prior to the arrival of medical personnel and/or law enforcement officers. The post-dispatch instructions 216 help to stabilize the situation, and to expedite the work of emergency responders at the scene. Post-dispatch instructions may include, for example, "do not disturb anything at the scene, including weapons, tools, or objects found nearby," "stay on the line and I'll tell you exactly what to do next," and the like.

Figure 3:
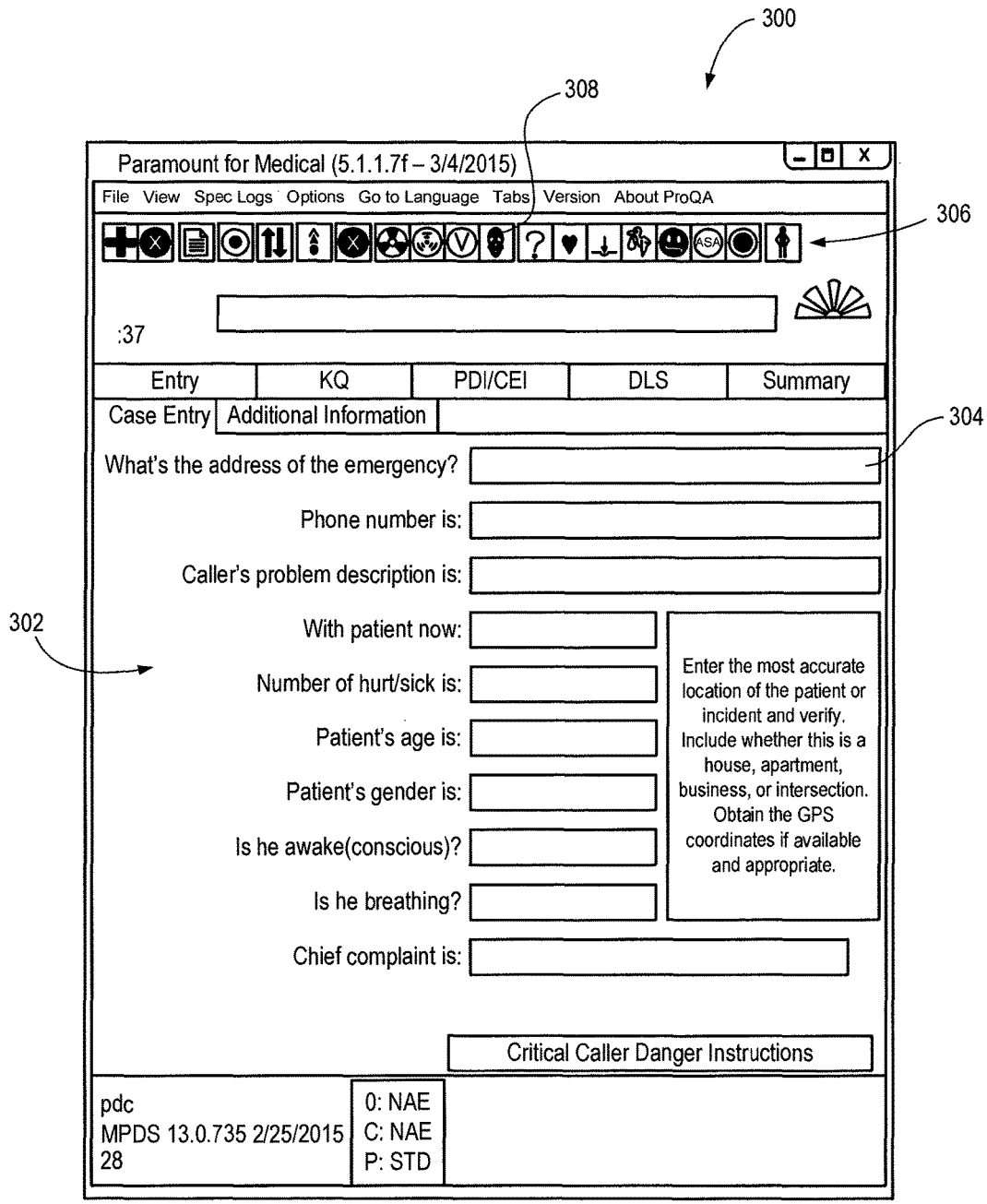
FIG. 3 is a user interface of an emergency medical dispatch system, according to one embodiment.

FIG. 3 depicts a user interface 300 of an emergency medical dispatch system, according to one embodiment. The emergency medical dispatch system user interface 300 allows a dispatcher to interface with the emergency medical dispatch protocol. The illustrated user interface 300 is shown traversing a case entry protocol 202 of the emergency medical dispatch protocol 108 (described above with reference to FIG. 2). The emergency medical dispatch protocol may present inquiries 302 (or questions) via the emergency medical dispatch system user interface 300. The inquiries 302 are provided for the dispatcher to relay to the caller to gather information regarding the reported incident or emergency. The dispatcher and/or the emergency medical dispatch system may gather the information in the form of caller responses to the inquiries 302. The dispatcher may input the responses of the caller to the inquiries into response fields 304 provided by the user interface 300. The response fields 304 may include, for example, any of a number of appropriate input field types, including but not limited to text fields, text boxes, menus, drop-down menus, drop-down selection boxes, lists, buttons, check boxes, radio buttons, and/or hybrid fields. For example, a text field for identifying the problem may allow for free-form input but also provide a list of suggestions to the dispatcher that can be inserted into the text field by clicking and/or double-clicking an entry in the list. The response fields 304 may correspond to information indicative of one or more responses of the caller to the inquiries 302. In some embodiments, the inquiries 302 may change from an interrogative form to an assertional form after a response has been entered and/or when a cursor is not in the corresponding response field 304.

The caller responses are relayed from the caller to the dispatcher, typically over the telephone. Information from the caller responses may be input into the system by the dispatcher and may be used by the emergency medical dispatch protocol to determine subsequent inquiries 302 and instructions to present to the dispatcher. The caller response information may indicate the caller's observations of the incident and/or current situation. The emergency medical dispatch system may use the caller response information to generate an emergency dispatch response by properly trained emergency responders. The information gathered from the caller responses may be used by the determinant value calculator to calculate a determinant value that can be communicated to the emergency responders. Additional details relating to emergency medical dispatch protocols and user interfaces to interact with the same can be found in the earlier referenced U.S. patents.

The system user interface 300 may also provide one or more diagnostic tool launch input components 306. As illustrated, one or more buttons may be provided on the user interface 300 as diagnostic tool launch input components 306. As will be appreciated by a person of ordinary skill, the diagnostic tool launch input components 306 may comprise a component other than a button, including familiar user interface components such as a drop-down menu, a drop-down selection box, a list, a checkbox, and a radio button. The diagnostic tool launch input components 306 enable the dispatcher to launch a particular diagnostic tool. Although the dispatch protocol may automatically initiate a diagnostic tool based on dispatcher-entered input indicative of one or more responses of the caller, the diagnostic tool launch input components 306 provide a way for the dispatcher to manually (e.g., anytime, at the dispatcher's discretion) initiate a diagnostic tool.

In the embodiment illustrated in FIG. 3, the user interface 300 provides a chemical suicide diagnostic tool launch input component 308. As shown, the chemical suicide diagnostic tool launch input component 308 may comprise a button on the emergency medical dispatch system user interface 300. The button may include an icon, such as an image of a skull and crossbones, to indicate that the button is the chemical suicide diagnostic tool launch input component 308 that manually initiates the chemical suicide diagnostic tool. In another embodiment, the button may include a label to convey that the button is the chemical suicide diagnostic tool launch input component 308.

Figure 4A:
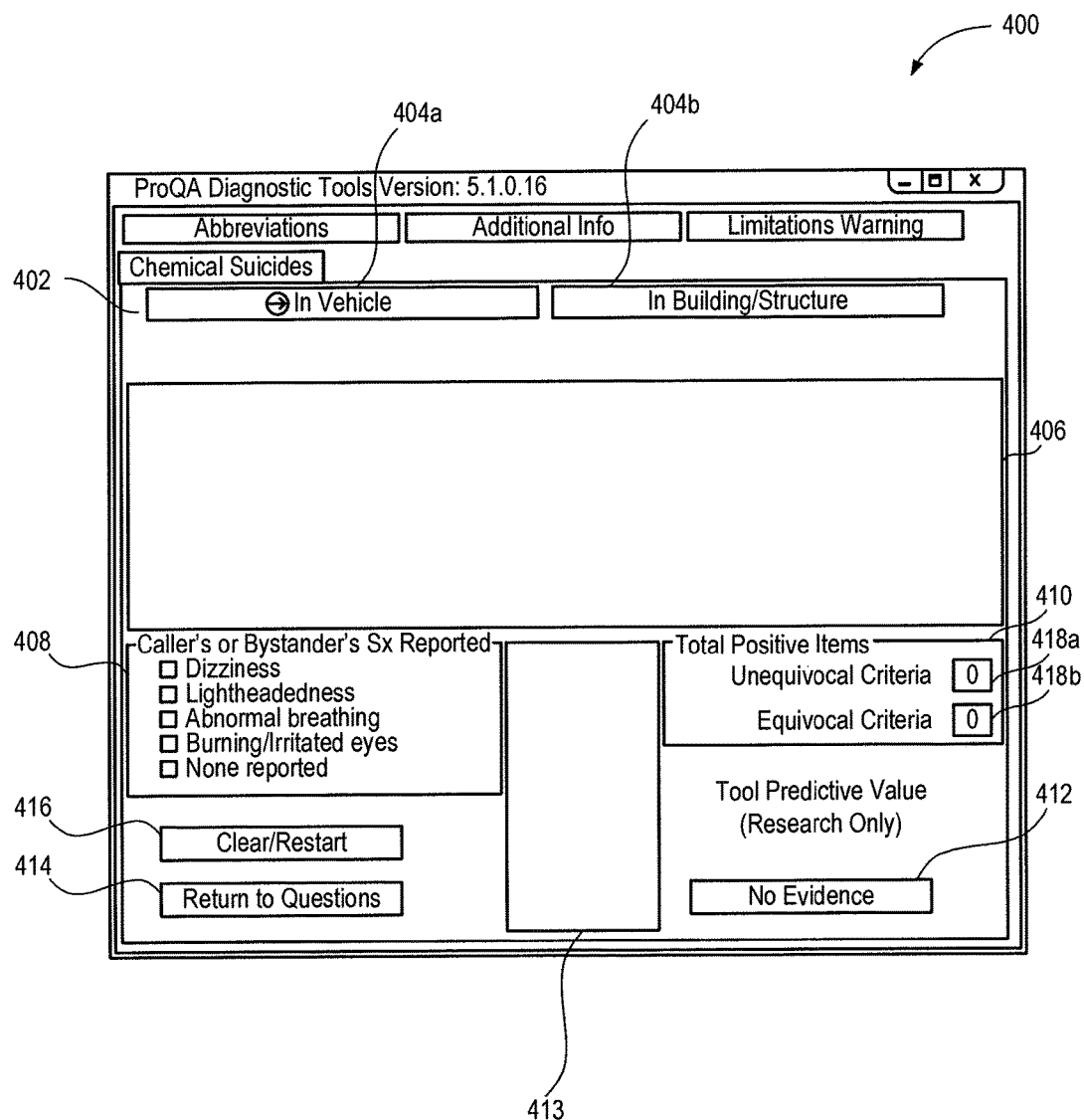
FIGS. 4A-4C illustrate a chemical suicide diagnostic tool user interface according to one embodiment.
Figure 4B:
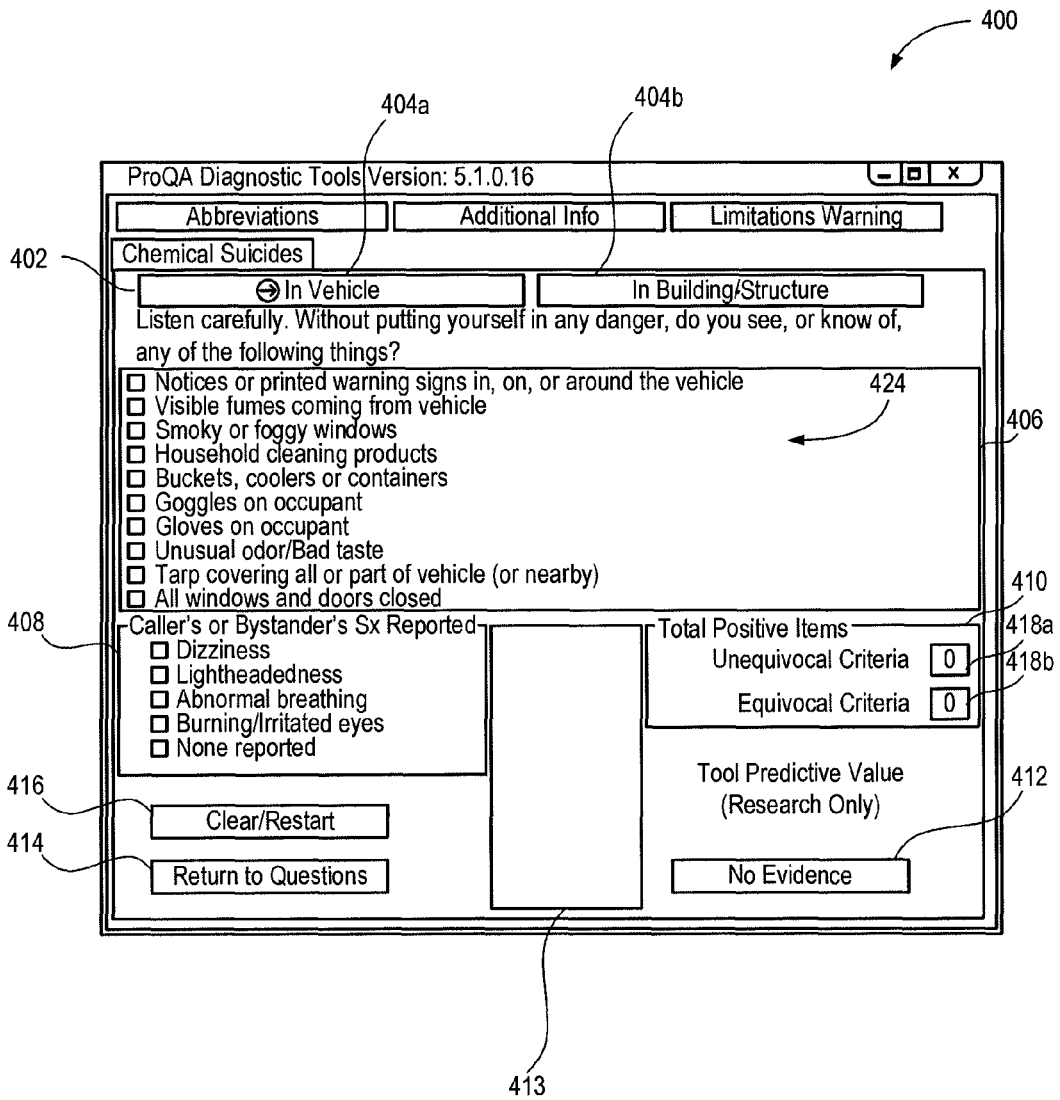
Figure 4C:
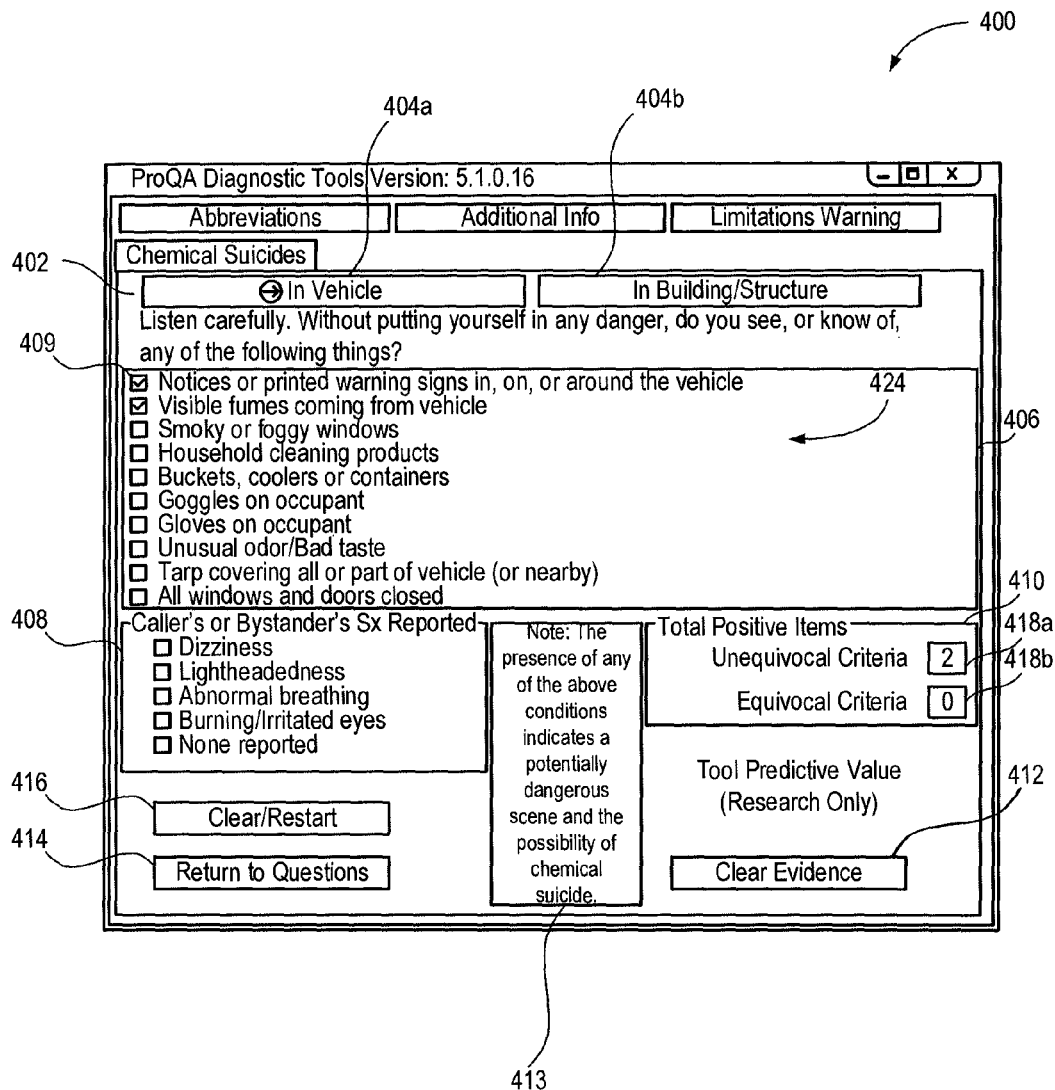

FIGS. 4A-4C illustrate a chemical suicide diagnostic tool user interface 400 according to one embodiment. Referring collectively to FIGS. 4A-4C, the diagnostic tool user interface 400 provides one or more instructions 402 to the dispatcher, structure classification input components 404a, 404b, an observations pane 406, a bystander symptom pane 408, a criteria summary pane 410, a recommendation field 412, an instruction pane 413, a return input component 414, and a reset input component 416.

The diagnostic tool user interface 400 is configured to assist a dispatcher in determining the likelihood that a chemical suicide has occurred. When an emergency caller reports that a victim is suspected to have committed or currently is committing chemical suicide, or otherwise reports observations that raise concern that the victim may have committed chemical suicide, the appropriate level of emergency response may depend largely on the likelihood that a chemical suicide has occurred. A difficulty arises in that often emergency callers are not skilled in identifying indicators that are factors used in determining or assessing the likelihood that a chemical suicide has occurred. The caller's lack of skill may present a safety concern, as the caller may fail to recognize the hazardous situation and enter the structure where the victim is. Similarly, the dispatcher may lack skill and experience to properly inquire and guide the caller in identifying and weighing indicators that are factors used in determining or assessing the likelihood that the victim has committed chemical suicide. In such case, the dispatcher's questions may cause the caller to enter into the dangerous space.

The diagnostic tool user interface 400, according to one embodiment of the present disclosure, may provide a pre-scripted interrogation of questions that help identify indicators that can be used to determine whether a chemical suicide has occurred. Indicators may include evidence observable at the scene, symptoms the caller and other bystanders are experiencing and/or other signs indicative of a chemical suicide. The diagnostic tool user interface 400 receives input corresponding to, or otherwise indicative of, the various identified indicators and uses the input to determine a likelihood that the victim is committing or has committed chemical suicide. The determination can be conveyed to the dispatcher via the diagnostic tool user interface 400 and/or conveyed to the emergency dispatch system. The manner by which the chemical suicide diagnostic tool can aid in determining the likelihood of chemical suicide will be made apparent by the following description of the illustrated embodiment of the diagnostic tool user interface 400.

The diagnostic tool user interface 400 may present one or more instructions intended to guide the dispatcher in using the tool. In the illustrated embodiment, the diagnostic tool user interface 400 provides an instruction 402 to request that the dispatcher classify the location into a structure category. Chemical suicide happens when chemicals are combined and inhaled in an enclosed space, such as a car or a building. The indicators of a chemical suicide may be different depending on what structure it occurs in. Accordingly, the diagnostic tool may function differently based on the structure in which the victim is. Location information of the victim may be communicated to the diagnostic tool by the emergency dispatch system, if the location information was previously obtained during processing of the call. The diagnostic tool user interface 400 also provides one or more structure classification input components 404a, 404b to allow the dispatcher to provide the information to the diagnostic tool. As can be appreciated, the dispatcher may need to ask the caller the structure in which the victim is if this information is not known. However, the configuration of the instruction 402 and structure classification input components 404a, 404b of the diagnostic tool user interface 400 provide intuitive guidance to the dispatcher to gather and/or provide information to the diagnostic tool concerning the victim's location.

In the illustrated embodiment, the structure classification input components 404a, 404b are buttons that the dispatcher can click to quickly and efficiently designate the structure in which the chemical suicide occurred. FIG. 4A illustrates the diagnostic tool user interface 400 prior to the dispatcher providing structure classification input to the diagnostic tool. The structure classification input components 404a, 404b include a label to clearly indicate to the dispatcher the information that will be entered by operating the button. For example, a first structure classification input component 404a includes a label "in vehicle" to indicate that clicking on the input component 404a enters information to the diagnostic tool that the victim is in a vehicle. A second structure classification input component 404b includes a label "in building/structure" to indicate that clicking on the input component 404b enters information to the diagnostic tool that the victim is in a building or structure. As can be appreciated, in another embodiment, the structure classification input components 404a, 404b are not limited to buttons and may include, for example, familiar user interface components, including but not limited to text fields, text boxes, menus, drop-down menus, drop-down selection boxes, lists, buttons, check boxes, and radio buttons, or any combination thereof.

The observations pane 406 presents one or more possible indicators 424 (FIG. 4B) of a chemical suicide to the dispatcher. The possible indicators 424 may include questions intended to be relayed by the dispatcher to the caller, to aid the dispatcher in guiding the caller to identify evidence that the victim has committed chemical suicide. The possible indicators 424 may also include questions directed solely to the dispatcher. FIG. 4B illustrates the diagnostic tool user interface 400 presenting a list of possible indicators 424 in the observations pane 406. In the illustrated embodiment, the possible indicators 424 are presented in a list. As can be appreciated, other presentation forms are possible, including but not limited to presenting the possible indicators serially.

The possible indicators 424 generally may relate to typical evidence found around the scene of a chemical suicide. This evidence may be different depending on the structure in which the victim is. For example, a chemical suicide in a vehicle may appear different from chemical suicide in a house. Further, in order to keep the caller out of danger, the evidence may be observable from a distance.

FIG. 4B illustrates possible indicators 424 for a chemical suicide occurring in a vehicle. As shown evidence of a chemical suicide may include but is not limited to "Notices or printed warning signs," "Visible fumes," "Smoky or foggy windows," Household cleaning products," "Buckets, coolers, or containers," "Goggles on occupant," "Gloves on occupant," "Unusual odor/Bad taste," "Tarp covering all or part of vehicle," "and "All windows and doors closed." The particular indicators presented, and the order in which they are presented, may depend on previously entered information. In another embodiment, the indicators presented may depend on whether the caller indicated other indicators are present. The diagnostic tool may traverse a logic tree that defines which indicators are presented in which order.

The bystander symptom pane 408 may also present one or more possible indicators 424. These indicators 424 may relate to symptoms the caller or other bystander is experiencing. The diagnostic tool user interface 400 may present the dispatcher with these indicators. The dispatcher may ask the caller if he/she is experiencing any of the symptoms. If the caller indicates that he/she is experiencing any of the symptoms, this may be further evidence that a chemical suicide did occur, and that the scene is potentially dangerous. The bystander symptom pane 408 may provide a way for the dispatcher to systematically and predictably determine if the caller is in danger. For example, symptoms may include "Dizziness," "Lightheadedness," "abnormal breathing," "burning/irritated eyes."

The response input components 409 provided by the user interface allow the dispatcher to quickly enter the caller's response to questions about possible indicators 424 presented in the observations pane 406 and the bystander symptom pane 408. In the illustrated embodiment, the response input components 409 are checkboxes that can be clicked by the dispatcher to indicate that the evidence was observed by the caller. For example, if the caller observes a certain indicator, the checkbox can be selected by the dispatcher and a checkmark would appear. As can be appreciated, in another embodiment, the response input components 409 are not limited to checkboxes and may include, for example, familiar user interface components, including but not limited to text fields, text boxes, menus, drop-down menus, drop-down selection, boxes, lists, buttons, and radio buttons, or any combination thereof.

As the indicators 424 are being gathered, the diagnostic tool may use the input to make a determination whether a chemical suicide has occurred. The determination may be presented in the recommendation field 412, as will be described below.

Based on the determination, the instruction pane 413 may present the dispatcher with specific information. For example, as illustrated in FIG. 4C, the diagnostic tool has determined that there is clear evidence, based on the input, of a chemical suicide. In the illustrated embodiment this results in a warning appearing in the instruction pane 413 indicating that the scene may be dangerous and that there is a possibility of a chemical suicide. The instruction pane 413 may also contain instructions that the dispatcher may relay to the caller to improve caller safety. The information in the instruction pane 413 may change based on the likelihood of a chemical suicide.

Referring again collectively to FIGS. 4A-4C, and specifically to FIG. 4C, the criteria summary pane 410 presents a concise tally of the type of positive indicators received that indicate the victim may have committed chemical suicide. The criteria summary pane 410 provides one or more tally fields 418a, 418b (collectively 418) that display a tally of one or more types of indicators. The tally displayed in a tally field 418a, 418b concisely communicates, for example to a dispatcher, a basis for a likelihood that a victim has committed chemical suicide. A tally can be an objective value that quantifies the factors in favor of a determination that a chemical suicide has occurred.

In the illustrated embodiment, a plurality of tally fields 418 are presented to provide tallies of indicators in a plurality of ranges of severity. Some of the indicators of chemical suicide may be more determinative than other indicators; i.e., certain indicators may or more strongly suggest a likelihood that the victim has committed chemical suicide. For example, some indicators may be unequivocal indicators because they may be substantially determinative that the victim has committed chemical suicide. A tally labeled "Unequivocal Criteria" may be helpful to indicate, for example to the dispatcher, the number of these unequivocal indicators that are present. A first tally field 418a may present the tally of unequivocal indicators. Other indicators may be equivocal indicators, which alone may not be indicative of a chemical suicide, but a number of minor indicators, cumulatively, may strongly suggest that a chemical suicide has occurred. A tally labeled "Equivocal Criteria" may be helpful to indicate the number of equivocal indicators. A second tally field 418b may present the tally of equivocal indicators. The plurality of tally fields 418 can provide insight to the dispatcher as to how and why the diagnostic tool reaches a particular result. The plurality of tally fields 418 can provide a summary explanation of why a chemical suicide is suspected.

As an example, the unequivocal indicators that may be substantially determinative and counted in the tally "Unequivocal Criteria" may include printed warning signs, visible fumes, door cracks sealed, household cleaning products, goggles on occupant, and tarp covering vehicle.

As another example, the equivocal indicators that cumulatively may strongly suggest a chemical suicide and may be counted in the tally "Equivocal Criteria" may include smoky/foggy windows, buckets or containers, gloves on occupant, unusual odor/bad taste, and all windows and doors closed.

In the illustrated embodiment, the tally fields 418 provide a running tally during the progression of the diagnostic tool. A running tally may allow a dispatcher to anticipate a result of the diagnostic tool, enabling the dispatcher to prepare for the next steps in processing the emergency call.

The recommendation field 412 provides an indication to the dispatcher of a recommendation and/or a determination made by the diagnostic tool as to whether the victim has committed or is currently committing chemical suicide. In FIG. 4C, the recommendation field 412 presents an indication stating "Clear Evidence" to indicate that the diagnostic tool has determined that there is significant evidence, and/or a high likelihood, that a chemical suicide has been committed. The recommendation field 412 may also present an indication stating "Strong Evidence" to indicate that the diagnostic tool has determined that there is some evidence of a chemical suicide. The recommendation field 412 may also present an indication stating "Partial Evidence" to indicate that the diagnostic tool has determined that there is little evidence, but still a possibility, of a chemical suicide. The recommendation field 412 may also present an indication stating "No Evidence" to indicate that there is not sufficient evidence, or no determined or discovered evidence, to determine that there was a chemical suicide. As can be appreciated, other recommendations are possible, including but not limited to "NEGATIVE" to indicate that the victim has not committed chemical suicide.

A scoring formula may be included to score the criteria and make a determination of the recommendation to present. As an example, the following scoring formula may be used by the tool to determine a recommendation to present in the recommendation field 412:

Clear Evidence if:
Two Unequivocal Criteria indicators are present, OR
Three Equivocal Criteria indicators are present, OR
One Unequivocal Criteria indicator and one or more Unequivocal Criteria indicators are present.
Strong Evidence if:
One Unequivocal Criteria indicator is present,
OR
Two Equivocal Criteria indicators are present.
No Evidence if:
No Unequivocal Criteria and up to one Equivocal Criteria indicators are present.

Other scoring formulas may be used. The scoring formulas may also evolve, changing over time as accuracy of the prediction of outcomes is assessed and improvements are made in diagnosing chemical suicide.

A return input component 414 is also presented to the dispatcher by the diagnostic tool user interface 400 to close the diagnostic tool and/or diagnostic tool user interface 400, and return processing and/or control to the medical dispatch protocol. In the depicted embodiment, the return input component 414 is provided as a button that the user can click on and that is labeled "Return to Questions." The dispatcher clicks the return input component 414 button to close the chemical suicide diagnostic tool. In another embodiment, the return input component 414 may also signal to the diagnostic tool to transfer the recommendation and/or the information provided concerning the victim's diagnostic instruction responses to the emergency medical dispatch protocol and/or determinant value calculator, prior to the diagnostic tool closing.

A reset input component 416 is also provided by the diagnostic tool user interface 400 of FIGS. 4A-4C to allow a dispatcher to reset the diagnostic tool. The reset input component 416 may clear all dispatcher-entered input from the diagnostic tool user interface 400 and/or the diagnostic tool. The reset input component 416 also moves progression along the logic tree back to the beginning, essentially starting the diagnostic tool over.

Figure 5:
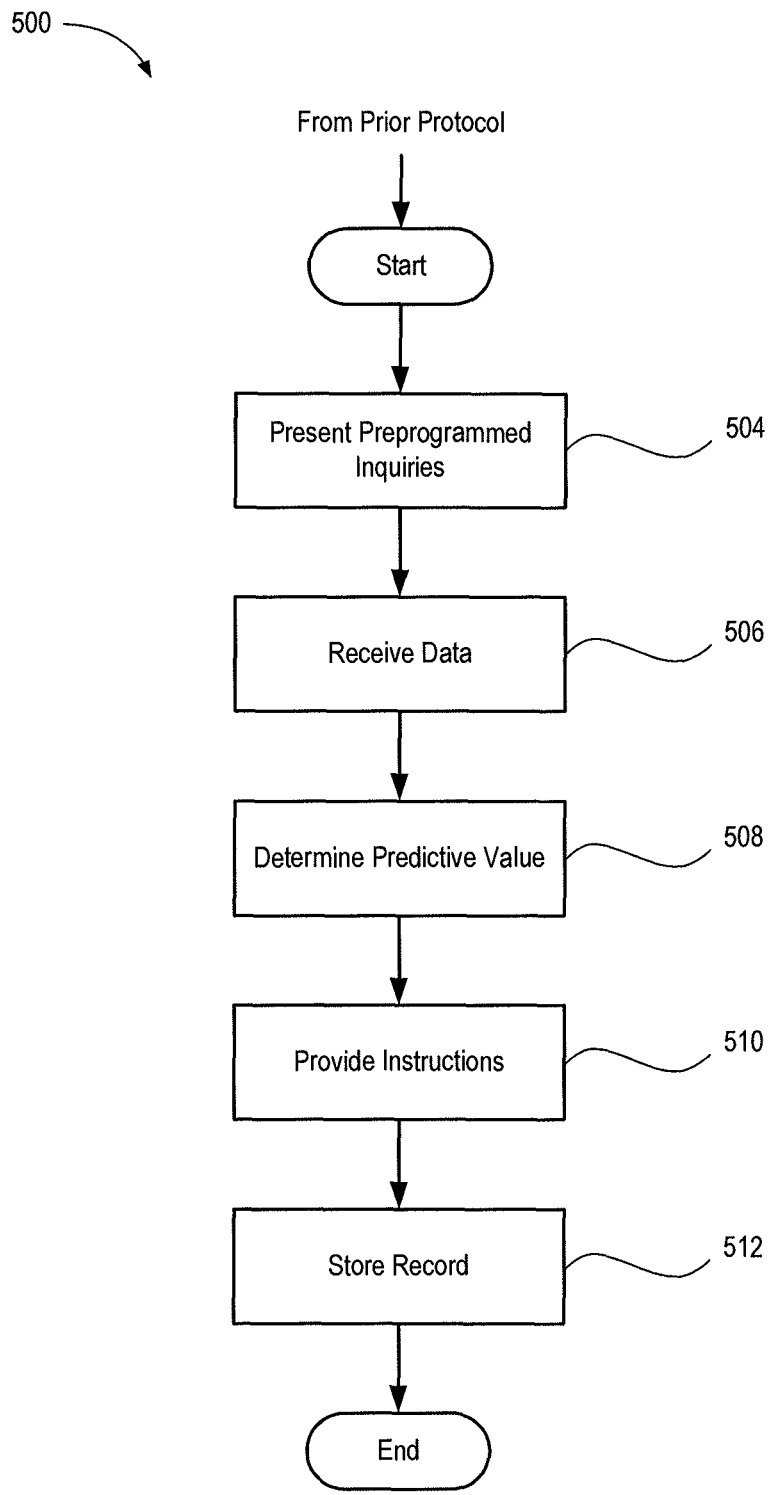
FIG. 5 is a high-level flow diagram of a method implemented by a chemical suicide dispatch protocol for a chemical suicide diagnostic tool, according to one embodiment.

FIG. 5 is a high-level flow diagram of a method 500 implemented by a chemical suicide dispatch protocol for a chemical suicide diagnostic tool, according to one embodiment. The chemical suicide diagnostic tool may be initiated (e.g., launched) from within an emergency dispatch protocol. The emergency dispatch protocol may automatically launch the tool based on input received by the emergency dispatch protocol indicating that the victim may have committed chemical suicide. The chemical suicide diagnostic tool may also be launched manually, as desired, by the dispatcher. Upon launching, the chemical suicide diagnostic tool may present a user interface.

The user interface may present 504 preprogrammed inquiries according to a pre-scripted interrogation. The preprogrammed inquiries may be targeted to ascertain the likelihood of a chemical suicide while keeping the caller and other bystanders safe. Data is received 506 from the dispatcher, as relayed from the caller, following the preprogrammed inquiries asked to the caller by the dispatcher. The data received 506 may correspond to caller responses to the preprogrammed inquiries. The data may be used to determine subsequent questions, and/or to determine instructions to provide to the dispatcher. The received data is also used by the diagnostic tool to determine 508 the likelihood of a chemical suicide and/or update an already determined predictive value. Intermediate predictive values may be produced as information is received and processed, and the final predictive value may be determined after all information is received and processed.

The diagnostic tool may provide 510 appropriate instructions to be relayed to the caller by the dispatcher. The instructions may comprise post-dispatch instructions for the caller to help stabilize or otherwise ameliorate a situation, to improve scene safety, and to expedite the work of emergency responders at the scene. A database may be accessed to produce appropriate instructions. Records of the calls are stored 512 for historical reports, for review and analysis of dispatcher performance, and for continued quality assurance control. A record of a call may include but is not limited to inquiries, responses, and predictive values.

Figure 6:
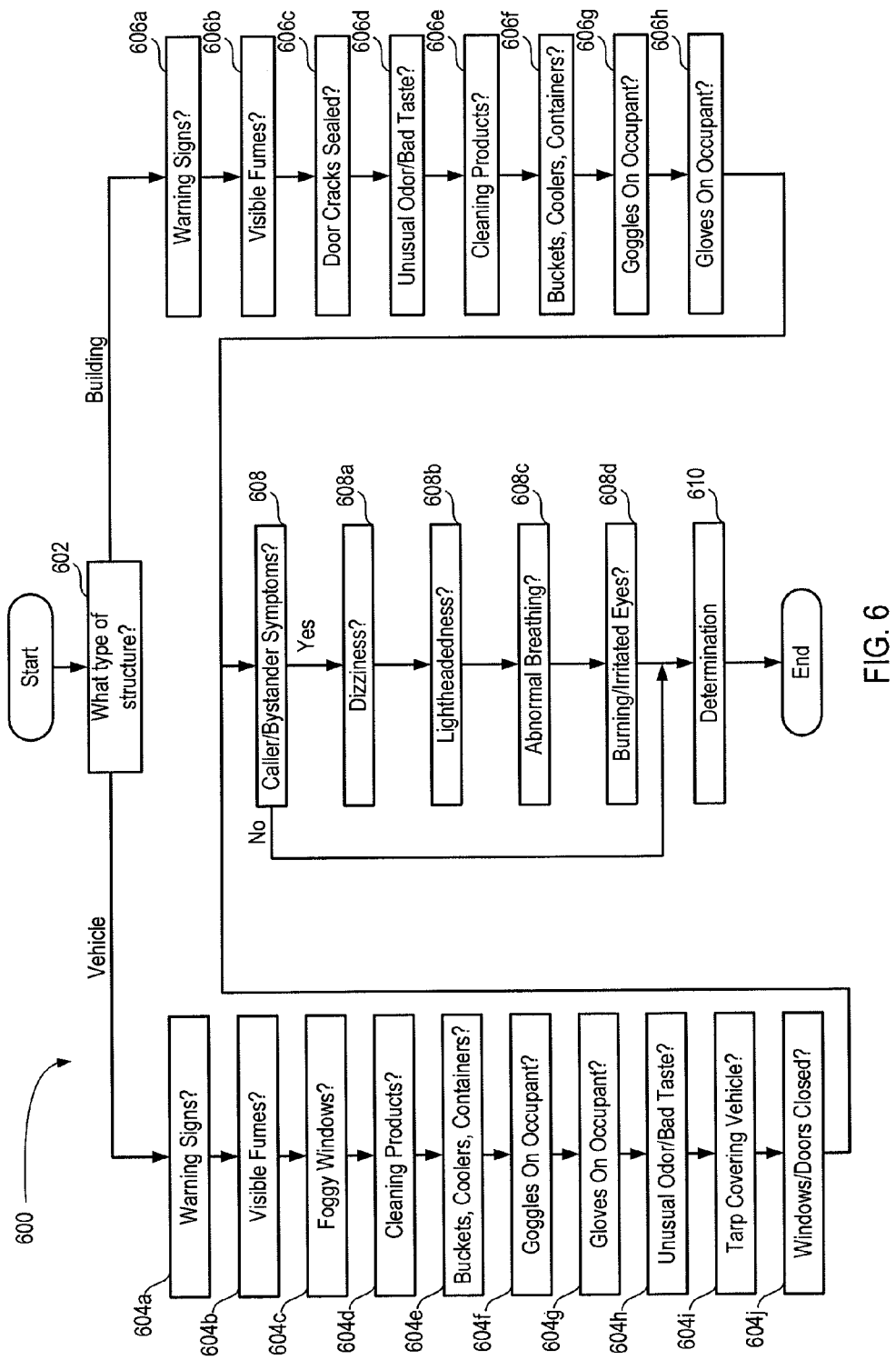
FIG. 6 is a detailed flow diagram of a method implemented by a chemical suicide dispatch protocol for a chemical suicide diagnostic tool, according to one embodiment.

FIG. 6 is a detailed flow diagram of a method 600 implemented by a chemical suicide dispatch protocol for a chemical suicide diagnostic tool, according to one embodiment. The chemical suicide protocol is initialized, typically, from a prior protocol. In particular, the chemical suicide protocol may be launched from the case entry protocol. As can be appreciated, the chemical suicide protocol may be accessed in a variety of ways. In an embodiment, the chemical suicide protocol may initialize once the emergency dispatch protocol has traversed all or a portion of a case entry protocol and shunts to the chemical suicide protocol as the appropriate dispatch protocol for handling the chief complaint of the call. Also, an emergency dispatch protocol may automatically shunt to the chemical suicide protocol immediately upon receiving indication that a chemical suicide event is being reported.

The chemical suicide protocol may launch a chemical suicide diagnostic tool to predict the likelihood of a chemical suicide event. To predict the likelihood, the chemical suicide diagnostic tool may present to the dispatcher a series of preprogrammed inquiries. The preprogrammed inquiries may be considered a part of a pre-scripted interrogation that is based on a logic tree of the chemical suicide protocol. The flow diagram of FIG. 6 may be considered to portray a logic tree, according to one embodiment. The preprogrammed inquiries that are presented as part of a pre-scripted interrogation may depend on dispatcher-entered input as will be described. A pre-scripted interrogation may be considered to be a set of preprogrammed inquiries presented according to traversal of a path along the logic tree.

During a pre-scripted interrogation, the chemical suicide protocol may receive input from the dispatcher corresponding to instructions and preprogrammed inquiries, as was explained above with reference to FIGS. 4A-4C and FIG. 5. The input may be received substantially in real time, as the dispatcher provides the input. Alternatively, or in addition, the input may be received from the emergency dispatch system because information sought by the chemical suicide protocol may have previously been obtained from the dispatcher via the case entry protocol and/or another portion of the dispatch protocol. Alternatively, or in addition, the input may be received from another diagnostic tool. While explicit steps of receiving information are not depicted in FIG. 6, an ordinarily skilled artisan will recognize that input may be received at various points in the method 600 of the chemical suicide protocol.

The dispatcher-entered input relates to the emergency call and/or the reported incident. The dispatcher-entered input may affect the path along which the logic tree is traversed. Various paths through one embodiment of a logic tree of a chemical suicide protocol will now be described, including the corresponding preprogrammed inquiries and potential dispatcher-entered input that may be considered.

The dispatcher may be presented 602 with an option to specify the structure type in which the incident is occurring. This may prompt the dispatcher to ask the caller to specify the structure if he/she has not already done so. The chemical suicide protocol may present possible responses such as "In Vehicle" and "In Building/Structure." Input may be received by way of selectable buttons such as structure classification input component 404a and 404b (see FIG. 4), or other input methods.

If the response indicates the victim is in a vehicle, the dispatcher may be presented with a preprogrammed inquiry, "Without putting yourself in any danger, do you see, or know of, any of the following things?" The dispatcher may be presented 604a-604j with a list of chemical suicide indicators including "Notices or printed warning signs in, on, or around the vehicle," "Visible fumes coming from vehicle," "Smoky or foggy windows," "Household cleaning products," "Buckets, cooler, or containers," "Goggles on occupant," "Gloves on occupant," Unusual odor/bad taste," "Tarp covering all or part of vehicle (or nearby)," and "All windows and doors closed." The dispatcher can query the caller to see if any of the evidence can be seen, and then indicate, for example, that the evidence is at the scene by checking a checkbox.

Alternatively, if the response indicates a different structure type, the list of indicators presented may be different. For example, if the response indicates the victim is in a building/structure, the dispatcher may be presented 606a-606h with a list of chemical suicide indicators including similar indicators such as "Notices or printed warning signs in, on, or around the confined space," "Visible fumes coming out," "Household cleaning products," "Buckets, cooler, or containers," "Goggles on occupant," "Gloves on occupant," and "Unusual odor/bad taste," as well as different indicators including "Door cracks or opening sealed with tape clothing, towels or other materials." The dispatcher can query the caller to see if any of the evidence can be seen, and then indicate, for example, that the evidence is at the scene by checking a checkbox.

The dispatcher may be presented 608 with a preprogrammed inquiry, "Is the caller or any bystander reporting any symptoms?" If the response indicates that a bystander/caller has symptoms, the chemical suicide protocol may present 608a-608d possible symptoms, such as "dizziness," "Lightheadedness," "Abnormal breathing," and "Burning/Irritated eyes." The dispatcher can query the caller to see if any of the symptoms are present, and then indicate, for example, that the symptoms are present by checking a checkbox.

If the dispatcher enters input that the caller/bystander is not experiencing symptoms, or after the protocol receives the symptoms, the protocol may make a determination 610 of the likelihood that there has been a chemical suicide. As described above, the determination 610 whether the victim has committed chemical suicide may be based on one or more tallies of indicators in one or more categories or ranges of severity. The determination may be displayed to the dispatcher and/or communicated to the emergency dispatch protocol and/or emergency responders. It will be also understood that the determination step may occur after each step or dispatcher-entered input. Thereby, updating the determination in real time.

While specific embodiments and applications of the disclosure have been illustrated and described, it is to be understood that the disclosure is not limited to the precise configuration and components disclosed herein. Various modifications, changes, and variations apparent to those of skill in the art may be made in the arrangement, operation, and details of the methods and systems of the disclosure without departing from the spirit and scope of the disclosure.

What is claimed is:

1. A computer-implemented method to guide a dispatcher when communicating vocally with a caller via a communication device regarding an incident involving a victim of a possible chemical suicide, and for predicting the likelihood of the incident being a chemical suicide, the computer-implemented method comprising:
    presenting, on a dispatch center computer device, a pre-scripted interrogation comprising a plurality of preprogrammed inquiries for the dispatcher to ask the caller in order to systematically obtain a description of the incident involving the possible chemical suicide, wherein the description of the incident comprises caller responses to the plurality of preprogrammed inquiries, and wherein the preprogrammed inquiries of the pre-scripted interrogation include:
    asking the type of structure in which the possible chemical suicide occurred,
    asking about observable indicators of chemical suicide;
    receiving, on the dispatch center computer device, dispatcher-entered input representative of caller responses to the preprogrammed inquiries of the pre-scripted interrogation;
    determining automatically on the dispatch center computer device a predictive value based on dispatcher-entered input representative of caller responses to one or more of the preprogrammed inquires, wherein the predictive value represents the likelihood that a chemical suicide occurred; and
    determining a priority of the incident based, at least in part, on the predictive value.

2. The computer-implemented method of claim 1, wherein presenting the pre-scripted interrogation further comprises the dispatch center computer device traversing a path of a logic tree as the pre-scripted interrogation progresses, the logic tree configured to determine the preprogrammed inquiries to present as part of the pre-scripted interrogation based on caller responses to the preprogrammed inquiries.

3. The computer-implemented method of claim 1, further comprising providing preprogrammed inquiries to the dispatcher via a user interface on an output device of the dispatch center computer device.

4. The computer-implemented method of claim 1, further comprising providing preprogrammed inquiries to the dispatcher on a medium readable by the dispatcher.

5. The computer-implemented method of claim 1, further comprising determining from dispatcher-entered input whether there is a potentially dangerous scene.

6. The computer-implemented method of claim 1, wherein the preprogrammed inquiries of the pre-scripted interrogation include asking what symptoms the caller is experiencing.

7. The computer-implemented method of claim 1, wherein the preprogrammed inquiries of the pre-scripted interrogation differ based on the type of structure in which the possible chemical suicide occurred.

8. The computer-implemented method of claim 1, further comprising updating automatically on the dispatch center computer device the predictive value based on a response to the preprogrammed inquiry asking about observable indicators of chemical suicide.

9. The computer-implemented method of claim 1, further comprising providing post-dispatch instructions to the caller.

10. The computer-implemented method of claim 1, wherein some of the dispatcher-entered inputs are assigned greater weight than others in determining the predictive value.

11. The computer-implemented method of claim 10, wherein the dispatcher-entered inputs that are assigned greater weight are considered unequivocal criteria, and the dispatcher-entered inputs that are assigned less weight are considered equivocal criteria.

12. The computer-implemented method of claim 1, further comprising providing a recommendation field that presents the predictive value, wherein the predictive value is selected from the group consisting of clear evidence, strong evidence, and no evidence.

13. A computer system to guide a dispatcher when communicating with a caller vocally via a communication device regarding a victim of an incident involving a possible chemical suicide, and for predicting the likelihood of the incident being a chemical suicide, the computer system comprising:
    a processor;
    an output device in communication with the processor;
    an input device in communication with the processor; and
    a memory in communication with the processor, the memory comprising:
    a chemical suicide protocol comprising a logic tree that is configured to determine a predictive value, the chemical suicide protocol configured to
    present on the output device a pre-scripted interrogation comprising a plurality of preprogrammed inquiries for the dispatcher to ask the caller in order to systematically obtain a description of the incident involving the possible chemical suicide, wherein the description of the incident comprises caller responses to the plurality of preprogrammed inquiries, and wherein the preprogrammed inquiries of the pre-scripted interrogation include:
asking the type of structure the possible chemical suicide occurred,
asking about observable indicators of chemical suicide;
receive, via the input device, dispatcher-entered input corresponding to caller responses to the preprogrammed inquiries of the pre-scripted interrogation,
determine automatically on the dispatch center computer device a predictive value based on dispatcher-entered input representative of caller responses to one or more of the preprogrammed inquires, wherein the predictive value represents the likelihood that a chemical suicide occurred, and
determine a priority of the incident based, at least in part, on the predictive value.

14. The computer system of claim 13, wherein said pre-programmed inquiries of the pre-scripted interrogation are according to a path along the logic tree that is traversed based on responses to the preprogrammed inquiries.

15. The computer system of claim 13, the memory further comprising a user interface that is displayed on the output device and configured to facilitate presentation of preprogrammed inquiries and to facilitate receiving dispatcher-entered input.

16. The computer system of claim 13, wherein the protocol is configured to determine the predictive value by determining whether a response to the preprogrammed inquiry asking about observable indicators of chemical suicide indicates an incident involving a chemical suicide.

17. The computer system of claim 13, wherein the chemical suicide protocol is further configured to determine from dispatcher-entered input whether there is a potentially dangerous scene.

18. The computer system of claim 13, wherein the pre-programmed inquiries of the pre-scripted interrogation include asking what symptoms the caller is experiencing.

19. The computer system of claim 13, wherein the pre-programmed inquiries of the pre-scripted interrogation differ based on the type of structure in which the possible chemical suicide occurred.

20. The computer system of claim 13, wherein the protocol is further configured to update automatically on the dispatch center computer device the predictive value based on a response to the preprogrammed inquiry asking about observable indicators of chemical suicide.

21. The computer system of claim 13, wherein the protocol assigns some of the dispatcher-entered input greater weight than others in determining the predictive value.

22. A non-transitory computer-readable storage medium having stored thereon computer-readable instruction code for a dispatch center computer to perform a method to assist a dispatcher when communicating vocally with a caller via a communication device regarding a victim of an incident involving a possible chemical suicide, the method comprising:
presenting on a dispatch center computer device a pre-scripted interrogation comprising a plurality of preprogrammed inquiries for the dispatcher to ask the caller to systematically obtain a description of the incident, the description of the incident comprising caller responses to the plurality of preprogrammed inquiries, wherein the dispatch center computer device includes a logic tree configured to determine the preprogrammed inquiries of the pre-scripted interrogation and automatically determine a predictive value based on dispatcher-entered input representative of caller responses to one or more of the preprogrammed inquires, and wherein the plurality of preprogrammed inquiries of the pre-scripted interrogation include
asking the type of structure the possible chemical suicide occurred,
asking about observable indicators of chemical suicide;
receiving dispatcher-entered input on the dispatch center computer device representative of caller responses to the preprogrammed inquiries of the pre-scripted interrogation;
assigning on the dispatch center computer device a predictive value determined by the logic tree and the pre-scripted interrogation, wherein the predictive value represents a determined probability that the incident involves a chemical suicide; and
determining a priority of the incident based, at least in part, on the predictive value.

* * * * *